US011319321B2

(12) United States Patent
Van Roosbroeck et al.

(10) Patent No.: US 11,319,321 B2
(45) Date of Patent: May 3, 2022

(54) [1,2,4]TRIAZOLO[1,5-A]PYRIMIDINE COMPOUNDS AS PDE2 INHIBITORS

(71) Applicant: Janssen Pharmaceutica NV, Beerse (BE)

(72) Inventors: Yves Emiel Maria Van Roosbroeck, Antwerp (BE); Frans Alfons Maria Van den Keybus, Essen (BE); Adriana Ingrid Velter, Antwerp (BE); Petrus Jacobus Johannes Antonius Buijnsters, Etten-Leur (NL); Gary John Tresadern, Toledo (ES); Henricus Jacobus Maria Gijsen, Breda (NL)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/346,745

(22) PCT Filed: Oct. 31, 2017

(86) PCT No.: PCT/EP2017/077918
§ 371 (c)(1),
(2) Date: May 1, 2019

(87) PCT Pub. No.: WO2018/083101
PCT Pub. Date: May 11, 2018

(65) Prior Publication Data
US 2020/0055858 A1 Feb. 20, 2020

(30) Foreign Application Priority Data
Nov. 2, 2016 (EP) ..................................... 16196936

(51) Int. Cl.
C07D 487/04 (2006.01)
(52) U.S. Cl.
CPC ................................ C07D 487/04 (2013.01)
(58) Field of Classification Search
CPC .................................................. C07D 487/04
See application file for complete search history.

(56) References Cited

U.S. PATENT DOCUMENTS

| 7,449,465 | B2 | 11/2008 | Freyne et al. |
| 8,138,168 | B1 | 3/2012 | Jones et al. |
| 8,946,415 | B2 | 2/2015 | Bi et al. |
| 9,682,953 | B2 | 6/2017 | Kharul et al. |
| 2004/0014744 | A1 | 1/2004 | Haviv et al. |
| 2009/0259044 | A1 | 10/2009 | Kazantsev |
| 2014/0031547 | A1 | 1/2014 | Sheridan et al. |
| 2015/0307522 | A1 | 10/2015 | Gray et al. |

FOREIGN PATENT DOCUMENTS

| CA | 2979222 | 9/2016 |
| CN | 1938308 | 3/2007 |
| CN | 103958473 | 7/2014 |
| CN | 104302649 | 1/2015 |
| CN | 105566321 | 11/2016 |
| EP | 0941994 | 9/1999 |
| JP | 2007332061 | 12/2007 |
| JP | 2014503528 | 2/2014 |
| TW | 201619612 | 6/2016 |
| TW | I553011 | 10/2016 |
| WO | WO 93/00313 | 7/1993 |
| WO | WO 99/37304 | 7/1993 |
| WO | WO 2004/031148 | 4/2004 |
| WO | WO 2004108136 | 12/2004 |
| WO | WO 2005/063738 | 7/2005 |
| WO | WO 2006/034341 | 3/2006 |
| WO | WO 2006/034440 | 3/2006 |
| WO | WO 2006044687 | 4/2006 |
| WO | WO 2007/022225 | 2/2007 |
| WO | WO 2007113136 | 10/2007 |
| WO | WO 2008/048914 | 4/2008 |
| WO | WO 2009047514 | 4/2009 |
| WO | WO 2012/114222 | 8/2012 |
| WO | WO 2013/000924 | 1/2013 |
| WO | WO 2013134113 | 9/2013 |
| WO | WO 2015/130905 | 9/2015 |
| WO | WO 2015140055 | 9/2015 |
| WO | WO 2015/164508 | 10/2015 |
| WO | WO 2016/107602 | 7/2016 |
| WO | WO 2017/003894 | 1/2017 |
| WO | WO 2017/003895 | 1/2017 |
| WO | WO 2017/066705 | 4/2017 |
| WO | WO 2017157882 | 9/2017 |
| WO | WO 2017/076900 | 11/2017 |

(Continued)

OTHER PUBLICATIONS

International Search Report and Written Opinion—PCT/EP2016/076420.
International Search Report and Written Opinion—PCT/EP2017/077910.
International Search Report and Written Opinion—PCT/EP2017/077918.
International Search Report and Written Opinion—PCT/EP2017/077920.
Albensi et al. Exp Neurol. 2007, vol. 204A, pp. 1-13.
Alzheimer's Association. "Huntington's Disease." (2012). Accessed Mar. 29, 2019. Available from:< https://www.alz.org/alzheimers-dementia/what-is-dementia/types-of-dementia/huntington-s-disease >. (Year: 2012).
Alzheimer's Association. "What Is Alzheimer's?" (Jan. 2007). Accessed Mar. 29, 2019. Available from:< https://www.alz.org/alzheimers-dementia/what-is-alzheimers >. (Year: 2007).

(Continued)

Primary Examiner — Paul V Ward
(74) Attorney, Agent, or Firm — Yuriy P. Stercho

(57) ABSTRACT

The present invention relates to novel [1,2,4]triazolo[1,5-a]pyrimidin-yl derivatives as inhibitors of phosphodiesterase 2 (PDE2). The invention is also directed to pharmaceutical compositions comprising the compounds, to processes for preparing such compounds and compositions, and to the use of such compounds and compositions for the prevention and treatment of disorders in which PDE2 is involved, such as neurological and psychiatric disorders.

6 Claims, No Drawings

(56) References Cited

FOREIGN PATENT DOCUMENTS

| WO | WO 2018/083098 | 5/2018 |
|---|---|---|
| WO | WO 2018/083101 | 5/2018 |
| WO | WO 2018/083103 | 5/2018 |
| WO | WO 2018109198 | 6/2018 |

OTHER PUBLICATIONS

Barco et al., Expert Opin Ther Targets 2003, vol. 7, pp. 101-114.
Bergado and Almaguer Neural Plast. 2002, vol. 9, No. 4, pp. 217-232.
Buijnsters et al. "Structure-Based Design of a Potent, Selective, and Brain Penetrating PDE2 Inhibitor with Demonstrated Target Engagement" ACS Med Chem Lett. 2014, vol. 5(9), pp. 1049-1053.
Cooke and Bliss, Curr Opin Investig Drugs. 2005, vol. 6, No. 1, pp. 25-34.
Dyatkin A.B. et. al, Chirality 2002, vol. 14, pp. 215-219.
Francis et al. Physiol Rev. 2011, vol. 9, pp. 651-690.
Gomez Laurent et al. "PDE2 inhibition: Potential for the treatment of cognitive disorders" Bioorganic & Medicinal Chemistry Letters 2013, vol. 3, No. 24, pp. 6522-6527.
Knott, E.P., et al. "Phosphodiesterase Inhibitors as a Therapeutic Approach to Neuroprotection and Repair." International Journal of Molecular Sciences. (2017), vol. 18, Issue 696, pp. 1-38 of 38. (Year: 2017).
Lakics, V. et al. "Quantitative comparison of phosphodiesterase mRNA distribution in human brain and peripheral tissues" 2010 Neuropharmacol. vol. 59, pp. 367-374.
Muller, N., et al. "Tourette's syndrome: clinical features, pathophysiology, and therapeutic approaches." Dialogues Clin Neurosci. (2007), vol. 9, pp. 161-171. (Year: 2007).
National Institute of Environmental Health Sciences. "Parkinson's Disease." (Feb. 2014). Accessed Mar. 29, 2019. Available from:<https://www.niehs.nih.gov/health/topics/conditions/parkinson/index.cfm >. (Year: 2014).
Omori and Kotera Circ Res. 2007, vol. 100, pp. 309-327.
Perugi, G., et al. "Diagnosis and Treatment of Agoraphobia with Panic Disorder." CNS Drugs. (2007), 21 (9), pp. 741-764. (Year:2007).
Reisman, M. "PTSD Treatment for Veterans: What's Working, What's New, and What's Next." P&T. (Oct. 2016), vol. 41, No. 10 , pp. 623-634. (Year: 2016).
Rowan et al. Biochem Soc Trans. 2005, vol. 33, pp. 563-567.
"Schizophrenia." (Mar. 2015). Accessed Mar. 29, 2019. Available from: < https://www.nami.org/NAMI/media/NAMI-Media/Images/FactSheets/Schizophrenia-FS.pdf >. (Year: 2015).
"Substance-induced psychotic disorder." (Oct. 2005). Accessed Mar. 29, 2019. Available from: < http://www.minddisorders.com/Py-Z/Substance-induced-psychotic-disorder.html > . (Year: 2005).
Su et al. Angew. Chem. Int. Ed. 2015, vol. 54, pp. 12942-12946.
Sweeney, P. "Parkinson's disease." Cleveland Clinic. (May 2013). Accessed Mar. 29, 2019. Available from:< http://www .clevelandclinicmeded.com/medicalpubs/diseasemanagement/neurology/parkinsons-disease/ >. (Year: 2013).
Van Duinen et al., Curr Pharm Des. 2015, vol. 21, pp. 3813-3828.
Xu et al., Neurobiol Aging. 2015, vol. 36, pp. 955-970.
CAS 1240215-31-9, Sep. 8, 2010, Methanone, [5-[(diethylamino)methyl]-2-furanyl][3-[6-(methylsulfonyl)[1,2,4]triazolo[1,5-a]pyrimidin-7-yl]-1-piperidinyl].
CAS 1240208-98-3, Sep. 8, 2010, Methanone, (1,2-dimethyl-1H-benzimidazol-5-yl)[3-[6-(methylsulfonyl)[1,2,4]triazolo[1,5-a]pyrimidin-7-yl]-1-piperidinyl.
CAS 1240206-26-1, Sep. 8, 2010, 1-Piperidinecarboxylic acid, 3-[3-methyl-2-(3-methylphenyl)pyrazolo[1,5-a]pyrimidin-7-yl]-, 1,1-dimethylethyl ester.
CAS 1240201-99-3, Sep. 7, 2010, Benzoic acid, 4-[[3-[6-(methylsulfonyl)[1,2,4]triazolo[1,5-a]pyrimidin-7-yl]-1-piperidinyl]carbonyl]-, methyl ester.
CAS 1240195-90-7, Sep. 7, 2010, Methanone, (1,5-dimethyl-1H-pyrazol-4-yl)[3-[6-(methylsulfonyl)[1,2,4]triazolo[1,5-a]pyrimidin-7-yl]-1-piperidinyl].
CAS 1240195-65-6, Sep. 7, 2010, Methanone, [3-[6-(methylsulfonyl)[1,2,4]triazolo[1,5-a]pyrimidin-7-yl]-1-piperidinyl]-1H-pyrazol-3-yl.
CAS 1240193-46-7, Sep. 7, 2010, Methanone, [1-(4-methoxyphenyl)cyclopropyl][3-[6-(methylsulfonyl)[1,2,4]triazolo[1,5-a]pyrimidin-7-yl]-1-piperidinyl].
CAS 1240193-08-1, Sep. 7, 2010, 1-Piperidinecarboxylic acid, 3-[2-(3-methylphenyl)pyrazolo[1,5-a]pyrimidin-7-yl]-, 1,1-dimethylethyl ester.
CAS 1240192-13-5, Sep. 7, 2010, 1-Propanone, 3-(5-methyl-1H-pyrazol-1-yl)-1-[3-[6-(methylsulfonyl)[1,2,4]triazolo[1,5-a]pyrimidin-7-yl]-1-piperidinyl].
CAS 1240186-67-7, Sep. 7, 2010, 1-Propanone, 3-(1-ethyl-3,5-dimethyl-1H-pyrazol-4-yl)-1-[3-[6-(methylsulfonyl)[1,2,4]triazolo[1,5-a]pyrimidin-7-yl]-1-piperidinyl].
CAS 1240181-24-1, Sep. 7, 2010, Methanone, (5-methyl-1-propyl-1H-pyrazol-4-yl)[3-[6-(methylsulfonyl)[1,2,4]triazolo[1,5-a]pyrimidin-7-yl]-1-piperidinyl].
CAS 1240176-67-3, Sep. 7, 2010, 1-Butanone, 4-(1H-indol-3-yl)-1-[3-[6-(methylsulfonyl)[1,2,4]triazolo[1,5-a]pyrimidin-7-yl]-1-piperidinyl].
CAS 1240169-61-2, Sep. 7, 2010, Methanone, (1-ethyl-5-methyl-1H-pyrazol-4-yl)[3-[6-(methylsulfonyl)[1,2,4]triazolo[1,5-a]pyrimidin-7-yl]-1-piperidinyl].
CAS 1240169-40-7, Sep. 7, 2010, Ethanone, 2-(3,4-dimethoxyphenyl)-1-[3-[6-(methylsulfonyl)[1,2,4]triazolo[1,5-a]pyrimidin-7-yl]-1-piperidinyl].
CAS 1240166-99-7, Sep. 7, 2010, Methanone, [3-(1,1-dimethylethyl)-1-methyl-1H-pyrazol-5-yl][3-[6-(methylsulfonyl)[1,2,4]triazolo[1,5-a]pyrimidin-7-yl]-1-piperidinyl].
CAS 1240166-22-6, Sep. 7, 2010, Methanone, (2-methyl-1H-benzimidazol-6-yl)[3-[6-(methylsulfonyl)[1,2,4]triazolo[1,5-a]pyrimidin-7-yl]-1-piperidinyl].
CAS 1240165-13-2, Sep. 7, 2010, Methanone, [1-(4-chlorophenyl)cyclobutyl][3-[6-(methylsulfonyl)[1,2,4]triazolo[1,5-a]pyrimidin-7-yl]-1-piperidinyl].
CAS 1240153-22-3, Sep. 7, 2010, Methanone, (1-ethyl-3-methyl-1H-pyrazol-4-yl)[3-[6-(methylsulfonyl)[1,2,4]triazolo[1,5-a]pyrimidin-7-yl]-1-piperidinyl].
CAS 1240147-20-9, Sep. 7, 2010, 1-Piperidineacetamide, N-(3-ethoxypropyl)-3-[2-methyl-6-(3-methyl-5-isoxazolyl)pyrazolo[1,5-a]pyrimidin-7-yl].
CAS 1240146-72-8, Sep. 7, 2010, Pyrimido[1,2-a]benzimidazole, 4-[1-[[1-(2-propyn-1-yl)-1H-indol-3-yl]methyl]-3-piperidinyl].
CAS 1240140-89-9, Sep. 7, 2010, 1-Piperidinecarboxylic acid, 3-[2-(4-methylphenyl)pyrazolo[1,5-a]pyrimidin-7-yl]-, 1,1-dimethylethyl ester.
CAS 1240128-18-0, Sep. 7, 2010, Methanone, (3,4-dimethoxyphenyl)[3-[6-(methylsulfonyl)[1,2,4]triazolo[1,5-a]pyrimidin-7-yl]-1-piperidinyl].
CAS 1240127-92-7, Sep. 7, 2010, 1-Piperidinecarboxylic acid, 3-[2-(3-fluorophenyl)pyrazolo[1,5-a]pyrimidin-7-yl]-, 1,1-dimethylethyl ester.
CAS 1240115-42-7, Sep. 7, 2010, Methanone, (1-ethyl-1H-pyrazol-4-yl)[3-[6-(methylsulfonyl)[1,2,4]triazolo[1,5-a]pyrimidin-7-yl]-1-piperidinyl].
CAS 1240104-61-3, Sep. 7, 2010, 1-Piperidinecarboxylic acid, 3-(2-phenylpyrazolo[1,5-a]pyrimidin-7-yl)-,1,1-dimethylethyl ester.
CAS 1240102-95-7, Sep. 7, 2010, Methanone, [3-[6-(methylsulfonyl)[1,2,4]triazolo[1,5-a]pyrimidin-7-yl]-1-piperidinyl](4,5,6,7-tetrahydro-1H-indazol-3-yl).
CAS 1240096-26-7, Sep. 7, 2010, Ethanone, 2-(2,5-dimethoxyphenyl)-1-[3-[6-(methylsulfonyl)[1,2,4]triazolo[1,5-a]pyrimidin-7-yl]-1-piperidinyl].
CAS 1240096-02-9, Sep. 7, 2010, 1-Piperidinecarboxylic acid, 3-[3-(4-fluorophenyl)-2-methylpyrazolo[1,5-a]pyrimidin-7-yl], 1,1-dimethylethyl ester.
CAS 1240093-87-1, Sep. 7, 2010, Methanone, (2,3-dihydro-1,4-benzodioxin-6-yl)[3-[6-(methylsulfonyl)[1,2,4]triazolo[1,5-a]pyrimidin-7-yl]-1-piperidinyl].

(56) References Cited

OTHER PUBLICATIONS

CAS 1240091-60-4, Sep. 7, 2010, Methanone, (4-amino-5-chloro-2-methoxyphenyl)[3-[6-(methylsulfonyl)[1,2,4]triazolo[1,5-a]pyrimidin-7-yl]-1-piperidinyl].
CAS 1214610-92-0, Mar. 25, 2010, Methanone, (3-methyl-2-benzofuranyl)[3-[6-(methylsulfonyl)[1,2,4]triazolo[1,5-a]pyrimidin-7-yl]-1-piperidinyl].
CAS 1214601-85-0, Mar. 25, 2010, Methanone, [3-[6-(methylsulfonyl)[1,2,4]triazolo[1,5-a]pyrimidin-7-yl]-1-piperidinyl](4-methyl-5-thiazolyl).
CAS 1214591-56-6, Mar. 25, 2010, Methanone, [3-[6-(methylsulfonyl)[1,2,4]triazolo[1,5-a]pyrimidin-7-yl]-1-piperidinyl](1,4,5,6-tetrahydro-3-cyclopentapyrazolyl).
CAS 1214520-74-7, Mar. 25, 2010, 1-Piperidineacetamide, N,N-bis(1-methylethyl)-3-[2-methyl-6-(3-methyl-5-isoxazolyl)pyrazolo[1,5-a]pyrimidin-7-yl].
CAS 1214496-02-2, Mar. 25, 2010, 1-Propanone, 3-(5-methyl-1H-pyrazol-1-yl)-1-[3-[2-(trifluoromethyl)[1,2,4]triazolo[1,5-a]pyrimidin-7-yl]-1-piperidinyl].
CAS 1214486-88-0, Mar. 25, 2010, Methanone, (3,5-dimethyl-4-isoxazolyl)[3-[6-(methylsulfonyl)[1,2,4]triazolo[1,5-a]pyrimidin-7-yl]-1-piperidinyl].
CAS 1214449-93-0, Mar. 25, 2010, 1-Propanone, 3-(5-methyl-2-furanyl)-1-[3-(2-methylpyrazolo[1,5-a]pyrimidin-7-yl)-1-piperidinyl].
CAS 1214427-36-7, Mar. 25, 2010, Methanone, 5-isoxazolyl[3-[6-(methylsulfonyl)[1,2,4]triazolo[1,5-a]pyrimidin-7-yl]-1-piperidinyl].
CAS 1184920-74-8, Sep. 16, 2009, 1-Piperidinecarboxylic acid, 3-(6-cyano-2-methylpyrazolo[1,5-a]pyrimidin-7-yl)-, 1,1-dimethylethyl ester.
CAS 960201-98-3, Jan. 9, 2008, 1-Piperidinecarboxylic acid, 3-(2-methylpyrazolo[1,5-a]pyrimidin-7-yl)-,1,1-dimethylethyl ester.
CAS 960201-89-2, Jan. 9, 2008, 1-Piperidinecarboxylic acid, 3-[2-(1,1-dimethylethyl)pyrazolo[1,5-a]pyrimidin-7-yl]-, 1,1-dimethylethyl ester.
CAS 958718-11-1, Dec. 19, 2007, Ethanone, 2-(4-methoxyphenyl)-1-[3-[6-(methylsulfonyl)[1,2,4]triazolo[1,5-a]pyrimidin-7-yl]-1-piperidinyl].
CAS 958715-94-1, Dec. 19, 2007, 1-Piperidinecarboxylic acid, 3-[3-(4-methoxyphenyl)-2-methylpyrazolo[1,5-a]pyrimidin-7-yl], 1,1-dimethylethyl ester.
CAS 958709-70-1, Dec. 19, 2007, Ethanone, 2-(4-fluorophenyl)-1-[3-[6-(methylsulfonyl)[1,2,4]triazolo[1,5-a]pyrimidin-7-yl]-1-piperidinyl].
CAS 958707-04-5, Dec. 19, 2007, Methanone, (3,5-difluorophenyl)[3-[6-(methylsulfonyl)[1,2,4]triazolo[1,5-a]pyrimidin-7-yl]-1-piperidinyl].
CAS 958706-09-7, Dec. 19, 2007, Methanone, [3-[6-(methylsulfonyl)[1,2,4]triazolo[1,5-a]pyrimidin-7-yl]-1-piperidinyl][4-(2-propen-1-yloxy)phenyl].
CAS 958706-04-2, Dec. 19, 2007, Methanone, cyclopentyl[3-[6-(methylsulfonyl)[1,2,4]triazolo[1,5-a]pyrimidin-7-yl]-1-piperidinyl].
CAS 958699-24-6, Dec. 19, 2007, Methanone, [3-(1,1-dimethylethyl)-1-methyl-1H-pyrazol-5-yl][3-[2-(trifluoromethyl)[1,2,4]triazolo[1,5-a]pyrimidin-7-yl]-1-piperidinyl].
CAS 958618-14-9, Dec. 18, 2007, Methanone, [3-[6-(methylsulfonyl)[1,2,4]triazolo[1,5-a]pyrimidin-7-yl]-1-piperidinyl](4,5,6,7-tetrahydrobenzo[b]thien-3-yl).
CAS 958615-91-3, Dec. 18, 2007, Ethanone, 2-(3-methoxyphenyl)-1-[3-[6-(methylsulfonyl)[1,2,4]triazolo[1,5-a]pyrimidin-7-yl]-1-piperidinyl].
CAS 958615-85-5, Dec. 18, 2007, Ethanone, 2-(2-methoxyphenyl)-1-[3-[6-(methylsulfonyl)[1,2,4]triazolo[1,5-a]pyrimidin-7-yl]-1-piperidinyl].
CAS 958606-22-9, Dec. 18, 2007, 1-Propanone, 1-[3-[6-(methylsulfonyl)[1,2,4]triazolo[1,5-a]pyrimidin-7-yl]-1-piperidinyl]-2-phenyl-.
CAS 958606-21-8, Dec. 18, 2007, 1-Butanone, 1-[3-[6-(methylsulfonyl)[1,2,4]triazolo[1,5-a]pyrimidin-7-yl]-1-piperidinyl]-2-phenyl-.
CAS 958606-01-4, Dec. 18, 2007, Methanone, 4-thiazolyl(3-[1,2,4]triazolo[1,5-a]pyrimidin-7-yl-1-piperidinyl).
CAS 958605-43-1, Dec. 18, 2007, 1-Piperidinecarboxylic acid, 3-[2-(3,4-dimethoxyphenyl)pyrazolo[1,5-a]pyrimidin-7-yl], 1,1-dimethylethyl ester.
CAS 958603-00-4, Dec. 18, 2007, 1-Propanone, 3-(2-furanyl)-1-[3-[6-(methylsulfonyl)[1,2,4]triazolo[1,5-a]pyrimidin-7-yl]-1-piperidinyl].
CAS 958596-76-4, Dec. 18, 2007, Methanone, (3-[1,2,4]triazolo[1,5-a]pyrimidin-7-yl-1-piperidinyl)(3,4,5-trimethoxyphenyl).
CAS 958596-27-5, Dec. 18, 2007, Methanone, [3-[6-(methylsulfonyl)[1,2,4]triazolo[1,5-a]pyrimidin-7-yl]-1-piperidinyl]-2-pyridinyl.
CAS 958587-78-5, Dec. 18, 2007, Methanone, [4-methoxy-3-(1H-pyrazol-1-ylmethyl)phenyl](3-[1,2,4]triazolo[1,5-a]pyrimidin-7-yl-1-piperidinyl).
CAS 958586-33-9, Dec. 18, 2007, Ethanone, 2-(3-fluorophenyl)-1-[3-[6-(methylsulfonyl)[1,2,4]triazolo[1,5-a]pyrimidin-7-yl]-1-piperidinyl].
CAS 958586-25-9, Dec. 18, 2007, Methanone, [3-[6-(methylsulfonyl)[1,2,4]triazolo[1,5-a]pyrimidin-7-yl]-1-piperidinyl]-3-pyridinyl-.
CAS 958585-88-1, Dec. 18, 2007, Methanone, [5-(1,1-dimethylethyl)-3-methyl-2-furanyl][3-[6-(methylsulfonyl)[1,2,4]triazolo[1,5-a]pyrimidin-7-yl]-1-piperidinyl].
CAS 958585-13-2, Dec. 18, 2007, Methanone, (3,4-dimethoxyphenyl)[3-(2-methylpyrazolo[1,5-a]pyrimidin-7-yl)-1-piperidinyl].
CAS 958583-88-5, Dec. 18, 2007, Ethanone, 2-cyclopentyl-1-[3-[6-(methylsulfonyl)[1,2,4]triazolo[1,5-a]pyrimidin-7-yl]-1-piperidinyl].
CAS 958583-87-4, Dec. 18, 2007, 1-Propanone, 1-[3-[6-(methylsulfonyl)[1,2,4]triazolo[1,5-a]pyrimidin-7-yl]-1-piperidinyl]-3-phenyl-.
CAS 958583-82-9, Dec. 18, 2007, Methanone, cyclohexyl[3-[6-(methylsulfonyl)[1,2,4]triazolo[1,5-a]pyrimidin-7-yl]-1-piperidinyl].
CAS 958583-78-3, Dec. 18, 2007, Methanone, (2-fluorophenyl)[3-[6-(methylsulfonyl)[1,2,4]triazolo[1,5-a]pyrimidin-7-yl]-1-piperidinyl].
CAS 958573-20-1, Dec. 18, 2007, 1-Piperidinecarboxylic acid, 3-[2-methyl-3-(2-thienyl)pyrazolo[1,5-a]pyrimidin-7-yl], 1,1-dimethylethyl ester.
CAS 878693-18-6, Mar. 31, 2006, 1-Piperidinecarboxylic acid, 3-[2-(4-methoxyphenyl)pyrazolo[1,5-a]pyrimidin-7-yl], 1,1-dimethylethyl ester.
Cheng Qiong, Studies on synthesis and bioactivity of novel triazolopyrimidine derivatives, Chinese Doctoral Dissertations Full-text Database, Engineering Science and Technology I, vol. 04, pp. B014-196, 2009 (see English Abstract).
Tu Wen-long, Studies on structure-activity relationship of phosphodiesterase 2 inhibitors, Chinese Master's Theses Full-text Database, Engineering Science and Technology I, vol. 8, pp. B016-19, 2014 (see English Abstract).

[1,2,4]TRIAZOLO[1,5-A]PYRIMIDINE COMPOUNDS AS PDE2 INHIBITORS

CROSS REFERENCE TO RELATED APPLICATIONS

This application is the national stage of PCT Application No. PCT/EP2017/077918, filed Oct. 31, 2017, which claims priority from European Patent Application No. 16196936.5 filed Nov. 2, 2016, the entire disclosures of which are hereby incorporated by reference in their entirety.

FIELD OF THE INVENTION

The present invention relates to novel [1,2,4]triazolo[1,5-a]pyrimidin-yl derivatives as inhibitors of phosphodiesterase 2 (PDE2). The invention is also directed to pharmaceutical compositions comprising the compounds, to processes for preparing such compounds and compositions, and to the use of such compounds and compositions for the prevention and treatment of disorders in which PDE2 is involved, such as neurological and psychiatric disorders.

BACKGROUND OF THE INVENTION

Phosphodiesterases (PDEs) are a family of enzymes encoded by 21 genes and subdivided into 11 distinct families according to structural and functional properties. These enzymes metabolically inactivate widely occurring intracellular second messengers, 3',5'-cyclic adenosine monophosphate (cAMP) and 3',5'-cyclic guanosine monophosphate (cGMP). These two messengers regulate a wide variety of biological processes, including pro-inflammatory mediator production and action, ion channel function, muscle contraction, learning, differentiation, apoptosis, lipogenesis, glycogenolysis, and gluconeogenesis. They do this by activation of protein kinase A (PKA) and protein kinase G (PKG), which in turn phosphorylate a wide variety of substrates including transcription factors and ion channels that regulate innumerable physiological responses. In neurons, this includes the activation of cAMP and cGMP-dependent kinases and subsequent phosphorylation of proteins involved in acute regulation of synaptic transmission as well as in neuronal differentiation and survival. Intracellular concentrations of cAMP and cGMP are strictly regulated by the rate of biosynthesis by cyclases and by the rate of degradation by PDEs. PDEs are hydrolases that inactivate cAMP and cGMP by catalytic hydrolysis of the 3'-ester bond, forming the inactive 5'-monophosphate (Scheme A).

Scheme A

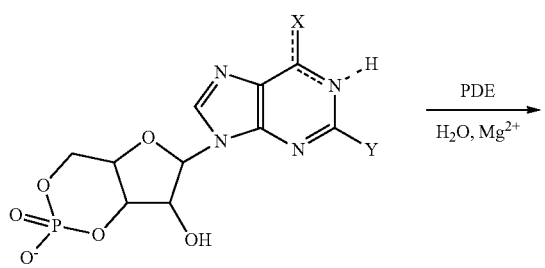

cAMP X = NH$_2$, Y = H
cGMP X = O, Y = NH$_2$

-continued

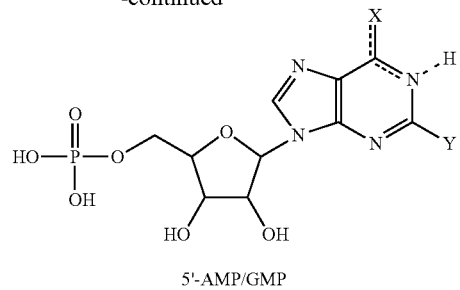

5'-AMP/GMP

On the basis of substrate specificity, the PDE families can be divided into three groups: i) the cAMP-specific PDEs, which include PDE4, 7 and 8; ii) the cGMP-selective enzymes PDE5, 6 and 9; and iii) the dual-substrate PDEs, PDE1, 2 and 3, as well as PDE10 and 11. Furthermore, PDEs are expressed differentially throughout the organism, including the central nervous system. Different PDE isozymes therefore may have different physiological functions. Compounds that inhibit selectively PDE families or isozymes may display particular therapeutic activity, fewer side effects, or both.

Phosphodiesterase 2A (PDE2A) inactivates intracellular signalling mechanisms reliant on cyclic nucleotide signalling mediated by cAMP and cGMP via their degradation (by hydrolizing the biologically relevant second messengers cAMP and cGMP into nonsignalling AMP and GMP, respectively). Such signalling pathways are known to play a role in the regulation of genes involved in the induction of synaptic plasticity.

The pharmacological inhibition of PDE2 therefore causes increased levels of synaptic plasticity (an underlying correlate of learning and memory), suggesting that PDE2A modulation may be a target for alleviating cognitive deficits seen in people suffering from disorders such as for example, schizophrenia, Alzheimer's disease, Parkinson's disease and other CNS disorders associated with cognitive dysfunction.

Phosphodiesterase 2A (PDE2A) is more abundantly expressed in the brain relative to peripheral tissues. The high expression of PDE2 in the limbic system (isocortex, hippocampus, amygdala, habenula, basal ganglia) suggests that PDE2 may modulate neuronal signalling involved in emotion, perception, concentration, learning and memory. Additionally, PDE2 is expressed in the nucleus accumbens, the olfactory bulb, the olfactory tubercle and the amygdala, supporting the suggestion that PDE2 may also be involved in anxiety and depression. (see for instance, Lakics, V. et al. (2010) Quantitative comparison of phosphodiesterase mRNA distribution in human brain and peripheral tissues. Neuropharmacol. 59, 367-374).

Additionally, PDE2 inhibitors have been shown to be beneficial in the reduction of oxidative stress-induced anxiety, supporting their use in the treatment of anxiety in neuropsychiatric and neurodegenerative disorders that involve oxidative stress, such as Alzheimer's disease, Parkinson's disease and multiple sclerosis.

PDE2 inhibitors have been shown to enhance long term potentiation of synaptic transmission and to improve memory acquisition and consolidation in the object recognition and in the social recognition tests in rats. Furthermore, PDE2 inhibitors have been shown to reverse the MK-801 induced working memory deficit in the T-maze in mice. PDE2 inhibitors have also been shown to display activity in forced swim test and light/dark box models; and to show anxiolytic-like effects in elevated plus-maze, hole-board and open-field tests and to prevent stress-induced changes in apoptosis and behaviour.

Thus, PDE2 inhibitors may be useful in the treatment of memory deficiency, cognitive disorders, anxiety, bipolar disorder and depression.

WO2015/164508 (Dart Neuroscience, LLC) discloses substituted [1,2,4]triazolo [1,5-a]pyrimidin-yl compounds as PDE2 inhibitors.

There is still a need for PDE2 inhibitor compounds with an advantageous balance of properties, for example with improved potency, better selectivity against PDE3 and/or PDE10, and/or better chemical or metabolic stability. The compounds of the present invention were found to exhibit a higher chemical stability profile and therefore were less amenable to racemization, yet displayed a similar or better activity profile than known PDE2 inhibitors

SUMMARY OF THE INVENTION

It is the object of the present invention to provide novel inhibitors of PDE2 that may be potentially useful in the treatment of diseases related to PDE2 enzyme activity.

Thus, the present invention is directed to compounds of Formula (IA)

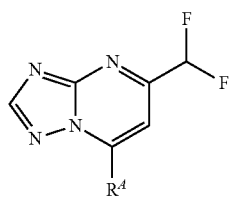

(IA)

and the stereoisomeric forms thereof, wherein
$R^A$ represents a radical (a) or (b):

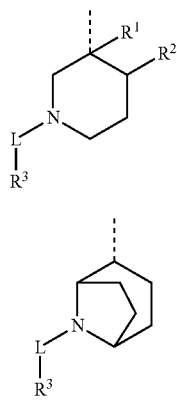

wherein
$R^1$ is hydrogen, fluoro, or methyl;
$R^2$ is hydrogen or $C_{1-6}$alkyl, in particular methyl; with the proviso that
$R^1$ is hydrogen or fluoro when $R^2$ is $C_{1-6}$alkyl, in particular methyl; and $R^1$ is methyl when $R^2$ is hydrogen or $C_{1-6}$alkyl;
L is selected from the group consisting of >CH$_2$, >CH(CH$_3$), >CH(CF$_3$) and —CH$_2$CH$_2$—; and $R^3$ is selected from the group consisting of $C_{1-4}$alkyl; aryl and Het; wherein
aryl represents a phenyl optionally substituted with one, two or three substituents, each independently selected from the group consisting of halo; —CN; $C_{1-4}$alkyl optionally substituted with 1, 2 or 3 independently selected halo substituents; and $C_{1-4}$alkyloxy optionally substituted with 1, 2 or 3 independently selected halo substituents;
Het is
(a) a 5-membered heteroaryl radical selected from thiophenyl and pyrazolyl, each optionally substituted with 1 or 2 independently selected $C_{1-4}$alkyl substituents; or
(b) a 6-membered heteroaryl radical selected from pyridyl and pyrimidinyl, each optionally substituted with 1 or 2 substituents, each independently selected from the group consisting of halo; —CN; $C_{1-4}$alkyl optionally substituted with 1, 2 or 3 independently selected halo substituents; $C_{3-6}$cycloalkyl; and 1-piperidinyl; or
(c) a 9- or 10-membered heteroaryl radical selected from the group consisting of 1H-indolyl, benzofuranyl, 1H-indazolyl, 1,3-benzothiazolyl, imidazo[1,2,-a]pyridinyl, and isoquinolinyl; each optionally substituted with a $C_{1-4}$alkyl substituent; or
(d) tetrahydropyranyl;
and the pharmaceutically acceptable salts and the solvates thereof.

Illustrative of the invention is a pharmaceutical composition comprising a pharmaceutically acceptable carrier and a compound of Formula (I) as described herein, or a pharmaceutically acceptable salt or a solvate thereof. An illustration of the invention is a pharmaceutical composition made by mixing a compound of Formula (I) as described herein, or a pharmaceutically acceptable salt or a solvate thereof, and a pharmaceutically acceptable carrier. Illustrating the invention is a process for making a pharmaceutical composition comprising mixing a compound of Formula (I) as described herein, or a pharmaceutically acceptable salt or a solvate thereof, and a pharmaceutically acceptable carrier.

Further illustrative of the invention are methods to enhance neuronal plasticity comprising administering to a subject in need thereof a therapeutically effective amount of a compound of Formula (I) as described herein, or a pharmaceutically acceptable salt or a solvate thereof, or pharmaceutical compositions described herein.

Exemplifying the invention are methods of treating a disorder mediated by the PDE2 enzyme, comprising administering to a subject in need thereof a therapeutically effective amount of a compound of Formula (I) as described herein, or a pharmaceutically acceptable salt or a solvate thereof, or pharmaceutical compositions described herein.

Further exemplifying the invention are methods of inhibiting the PDE2 enzyme, comprising administering to a subject in need thereof a therapeutically effective amount of a compound of Formula (I) as described herein, or a pharmaceutically acceptable salt or a solvate thereof, or pharmaceutical compositions described herein.

An example of the invention is a method of treating a disorder selected from the group consisting of neurological and psychiatric disorders, comprising administering to a subject in need thereof, a therapeutically effective amount of a compound of Formula (I) as described herein, or a pharmaceutically acceptable salt or a solvate thereof, or pharmaceutical compositions described herein.

An example of the invention is a method of treating a disorder selected from the group of neurological and psychiatric disorders selected from psychotic disorders and conditions; anxiety disorders; movement disorders; drug abuse; mood disorders; neurodegenerative disorders; disorders or conditions comprising as a symptom a deficiency in attention and/or cognition; disorders related to memory acquisition and consolidation; stroke; and autistic disorders, comprising administering to a subject in need thereof, a therapeutically effective amount of a compound of Formula (I) as described herein, or a pharmaceutically acceptable salt or a solvate thereof, or a pharmaceutically acceptable salt or a solvate thereof or pharmaceutical compositions described herein.

An example of the invention is a method of treating a disorder selected from the group consisting of neurological and psychiatric disorders comprising administering to a subject in need thereof, a therapeutically effective amount of a compound of Formula (I) as described herein or a pharmaceutically acceptable salt or a solvate thereof, or pharmaceutical compositions described herein.

An example of the invention is a method of treating a disorder selected from the group of neurological and psychiatric disorders selected from psychotic disorders and conditions; anxiety disorders; movement disorders; drug abuse; mood disorders; neurodegenerative disorders; disorders or conditions comprising as a symptom a deficiency in attention and/or cognition; disorders related to memory acquisition and consolidation; stroke; and autistic disorders, comprising administering to a subject in need thereof, a therapeutically effective amount of a compound of Formula (I) or a salt or a solvate thereof, or pharmaceutical compositions described herein.

Also exemplifying the invention is a compound of Formula (I) or a salt or a solvate thereof, or a pharmaceutical composition described herein, for use as a medicament.

Further exemplifying the invention is a compound of Formula (I) or a salt or a solvate thereof, or a pharmaceutical composition according to the invention for use in the treatment, prevention, amelioration, control or reduction of the risk of various neurological and psychiatric disorders associated with phosphodiesterase 2 dysfunction in a mammal, including a human, the treatment or prevention of which is affected or facilitated by the inhibition of phosphodiesterase 2.

An example of the invention is a compound of Formula (I) or a pharmaceutically acceptable salt or a solvate thereof according to the present invention or a pharmaceutical composition according to the invention for use in the treatment, prevention, amelioration, control or reduction of the risk of various disorders selected from psychotic disorders and conditions; anxiety disorders; movement disorders; drug abuse; mood disorders; neurodegenerative disorders; disorders or conditions comprising as a symptom a deficiency in attention and/or cognition; disorders related to memory acquisition and consolidation; stroke; and autistic disorder.

An example of the invention is a method of treating a disorder selected from the group consisting of Alzheimer's disease, mild cognitive impairment, senility, dementia, dementia with Lewy bodies, Down's syndrome, dementia associated with stroke, dementia associated with Parkinson's disease and dementia associated with beta-amyloid, preferably Alzheimer's disease, comprising administering to a subject in need thereof, a therapeutically effective amount of a compound of Formula (I) or a pharmaceutically acceptable salt of a solvate thereof, or pharmaceutical compositions described herein.

Another example of the invention is a compound of Formula (I) or a pharmaceutically acceptable salt or a solvate thereof described herein for use in treating: (a) Alzheimer's Disease, (b) mild cognitive impairment, (c) senility, (d) dementia, (e) dementia with Lewy bodies, (f) Down's syndrome, (g) dementia associated with stroke, (h) dementia associated with Parkinson's disease, (i) dementia associated with beta-amyloid, (j) depressive disorders and (k) anxiety disorders, in a subject in need thereof.

DETAILED DESCRIPTION OF THE INVENTION

Definitions

"$C_{1-4}$alkyl" as used herein alone or as part of another group, defines a saturated, straight or branched, hydrocarbon radical having, 1, 2, 3 or 4 carbon atoms, such as methyl, ethyl, 1-propyl, 1-methyl, butyl, 1-methyl-propyl, 2-methyl-1-propyl, 1,1-dimethylethyl and the like. The term "$C_{1-6}$alkyl" as used herein as a group or part of a group represents a straight or branched chain saturated hydrocarbon radical having from 1 to 6 carbon atoms such as the groups defined for $C_{1-4}$alkyl and n-pentyl, n-hexyl, 2-methylbutyl and the like. "$C_{1-4}$alkyloxy" shall denote an ether radical wherein $C_{1-4}$alkyl is as defined herein. "Halo" shall denote fluoro, chloro and bromo. "$C_{3-6}$cycloalkyl" shall denote cyclopropyl, cyclobutyl, cyclopentyl, and cyclohexyl.

Whenever the term "substituted" is used in the present invention, it is meant, unless otherwise indicated or is clear from the context, to indicate that one or more hydrogens, preferably from 1 to 3 hydrogens, or from 1 to 2 hydrogens, or 1 hydrogen, on the atom or radical indicated in the expression using "substituted" is replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Hereinbefore and hereinafter, the term "compound of formula (I)" is meant to include the addition salts, the solvates and the stereoisomers thereof.

The terms "stereoisomers" or "stereochemically isomeric forms" hereinbefore or hereinafter are used interchangeably.

The invention includes all stereoisomers of the compound of Formula (I) either as a pure stereoisomer or as a mixture of two or more stereoisomers.

Enantiomers are stereoisomers that are non-superimposable mirror images of each other. A 1:1 mixture of a pair of enantiomers is a racemate or racemic mixture. Diastereomers (or diastereoisomers) are stereoisomers that are not enantiomers, i.e. they are not related as mirror images. Therefore, the invention includes enantiomers, diastereomers, racemates. In the compounds according to the invention, bonds shown with a wedge of parallel lines ( ····|| ) represent bonds projected below the plane of the drawing, while bonds shown with a bold wedge (◥) represent bonds projected above the plane of the drawing.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Representative acids which may be used in the preparation of pharmaceutically acceptable salts include, but are not limited to, the following: acetic acid, 2,2-dichloro-acetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, trifluoromethylsulfonic acid, and undecylenic acid. Representative bases which may be used in the preparation of pharmaceutically acceptable salts include, but are not limited to, the following: ammonia, L-arginine, benethamine, benzathine, calcium hydroxide, choline, dimethylethanolamine, diethanolamine, diethylamine, 2-(diethylamino)-ethanol, ethanolamine, ethylene-diamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The names of the compounds of the present invention were generated according to the nomenclature rules agreed upon by the Chemical Abstracts Service (CAS) using Advanced Chemical Development, Inc., software (ACD/Name product version 10.01; Build 15494, 1 Dec. 2006 or ACD/ChemSketch product version 12.5; Build 47877, 20 Apr. 2011) or according to the nomenclature rules agreed upon by the International Union of Pure and Applied Chemistry (IUPAC) using Advanced Chemical Development, Inc., software (ACD/Name product version 10.01.0.14105, October 2006). In case of tautomeric forms, the name of the depicted tautomeric form of the structure was generated. The other non-depicted tautomeric form is also included within the scope of the present invention.

The present invention is directed to compounds of Formula (I) as defined hereinbefore and pharmaceutically acceptable salts and solvates thereof.

In an embodiment, the present invention is directed to compounds of Formula (I)

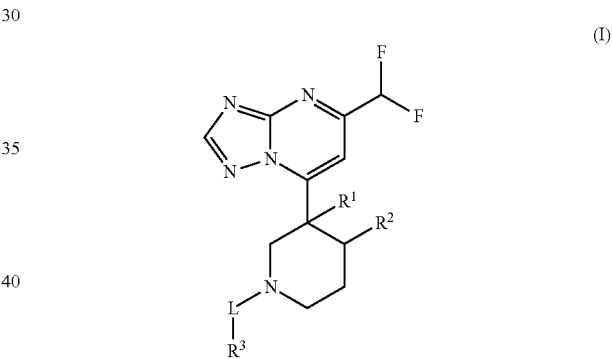

(I)

and the stereoisomeric forms thereof, wherein
$R^1$ is hydrogen, fluoro, or methyl;
$R^2$ is hydrogen or $C_{1-6}$alkyl, in particular methyl; with the proviso that
$R^1$ is hydrogen or fluoro when $R^2$ is $C_{1-6}$alkyl, in particular methyl; and $R^1$ is methyl when
$R^2$ is hydrogen or $C_{1-6}$alkyl;
L is selected from the group consisting of >CH$_2$, >CH(CH$_3$), >CH(CF$_3$) and —CH$_2$CH$_2$—; and
$R^3$ is selected from the group consisting of $C_{1-4}$alkyl; aryl and Het; wherein
aryl represents a phenyl optionally substituted with one, two or three substituents, each independently selected from the group consisting of halo; —CN; $C_{1-4}$alkyl optionally substituted with 1, 2 or 3 independently selected halo substituents; and $C_{1-4}$alkyloxy optionally substituted with 1, 2 or 3 independently selected halo substituents;
Het is
(a) a 5-membered heteroaryl radical selected from thiophenyl and pyrazolyl, each optionally substituted with 1 or 2 independently selected $C_{1-4}$alkyl substituents; or
(b) a 6-membered heteroaryl radical selected from pyridyl and pyrimidinyl, each optionally substituted with 1 or 2 substituents, each independently selected from the group consisting of halo; —CN; $C_{1-4}$alkyl optionally substituted with 1, 2 or 3 independently selected halo substituents; $C_{3-6}$cycloalkyl; and 1-piperidinyl; or (c) a 9- or 10-membered heteroaryl radical selected from the group consisting of 1H-indolyl, benzofuranyl, 1H-indazolyl, 1,3-benzothiazolyl, imidazo[1,2,-a]pyridinyl, and isoquinolinyl; each optionally substituted with a $C_{1-4}$alkyl substituent; or (d) tetrahydropyranyl;

and the pharmaceutically acceptable salts and the solvates thereof.

In a particular embodiment, the invention relates to a compound according to the Formula (I) as described herein, wherein $R^1$ is hydrogen, fluoro, or methyl;

$R^2$ is $C_{1-6}$alkyl, in particular methyl;

L is selected from the group consisting of >CH$_2$ and >CH(CH$_3$); and $R^3$ is selected from the group consisting of aryl and Het; wherein aryl represents a phenyl optionally substituted with one, two or three substituents, each independently selected from the group consisting of halo; —CN; $C_{1-4}$alkyl optionally substituted with 1, 2 or 3 independently selected halo substituents; and $C_{1-4}$alkyloxy optionally substituted with 1, 2 or 3 independently selected halo substituents;

Het is a 6-membered heteroaryl radical selected from pyridyl and pyrimidinyl, each optionally substituted with 1 or 2 substituents, each independently selected from the group consisting of halo; —CN; $C_{1-4}$alkyl optionally substituted with 1, 2 or 3 independently selected halo substituents; $C_{3-6}$cycloalkyl; and 1-piperidinyl.

In a particular embodiment, the invention relates to a compound according to the Formula (I) as described herein, wherein $R^1$ is hydrogen, fluoro, or methyl;

$R^2$ is methyl;

L is selected from the group consisting of >CH$_2$ and >CH(CH$_3$); and $R^3$ is a 6-membered heteroaryl radical selected from pyridyl and pyrimidinyl, each optionally substituted with 1 or 2 substituents, each independently selected from the group consisting of halo; —CN; $C_{1-4}$alkyl optionally substituted with 1, 2 or 3 independently selected halo substituents; $C_{3-6}$cycloalkyl; and 1-piperidinyl.

In a particular embodiment, the invention relates to a compound according to the Formula (I) as described herein, wherein $R^3$ is pyridyl optionally substituted with 1 or 2 substituents, each independently selected from the group consisting of halo; —CN; $C_{1-4}$alkyl optionally substituted with 1, 2 or 3 independently selected halo substituents; and $C_{3-6}$cycloalkyl.

In a particular embodiment, the invention relates to a compound according to the Formula (I) as described herein, wherein $R^3$ is pyridyl optionally substituted with 1 or 2 substituents, each independently selected from the group consisting of halo; $C_{1-4}$alkyl optionally substituted with 1, 2 or 3 independently selected halo substituents; and $C_{3-6}$cycloalkyl.

In a particular embodiment, the invention relates to a compound according to the Formula (I) as described herein, wherein $R^3$ is pyridyl substituted with 1 or 2 independently selected $C_{1-4}$alkyl substituents.

In a further embodiment, the invention relates to a compound according to the Formulae (A) or (I) as described herein, having the formula (I-a)

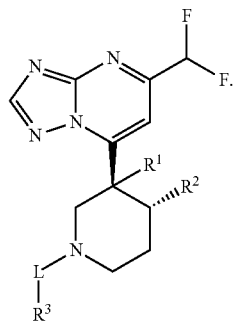

(I-a)

In an additional embodiment, the invention relates to a compound according to the Formulae (IA) or (I) as described herein, having the Formula (I-b)

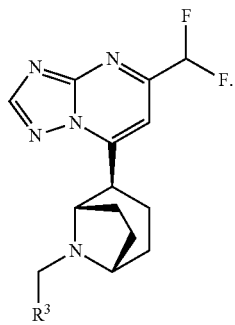

(I-b)

In a further embodiment, the invention relates to a compound of Formula (I-b) as defined herein, wherein $R^3$ is aryl or Het; wherein aryl represents a phenyl optionally substituted with one, two or three substituents, each independently selected from the group consisting of halo; —CN; $C_{1-4}$alkyl optionally substituted with 1, 2 or 3 independently selected halo substituents; and $C_{1-4}$alkyloxy optionally substituted with 1, 2 or 3 independently selected halo substituents; and Het is a 6-membered heteroaryl radical selected from pyridyl and pyrimidinyl, each optionally substituted with 1 or 2 substituents, each independently selected from the group consisting of halo; —CN; $C_{1-4}$alkyl optionally substituted with 1, 2 or 3 independently selected halo substituents; $C_{3-6}$cycloalkyl; and 1-piperidinyl.

In a particular embodiment, the invention relates to a compound according to the Formula (I-b) as described herein, wherein $R^3$ is phenyl optionally substituted with one, two or three substituents, each independently selected from the group consisting of halo; —CN; $C_{1-4}$alkyl optionally substituted with 1, 2 or 3 independently selected halo substituents; and $C_{1-4}$alkyloxy optionally substituted with 1, 2 or 3 independently selected halo substituents.

GENERAL SYNTHETIC PROCEDURES

Experimental Procedure 1

Reaction Scheme 1a

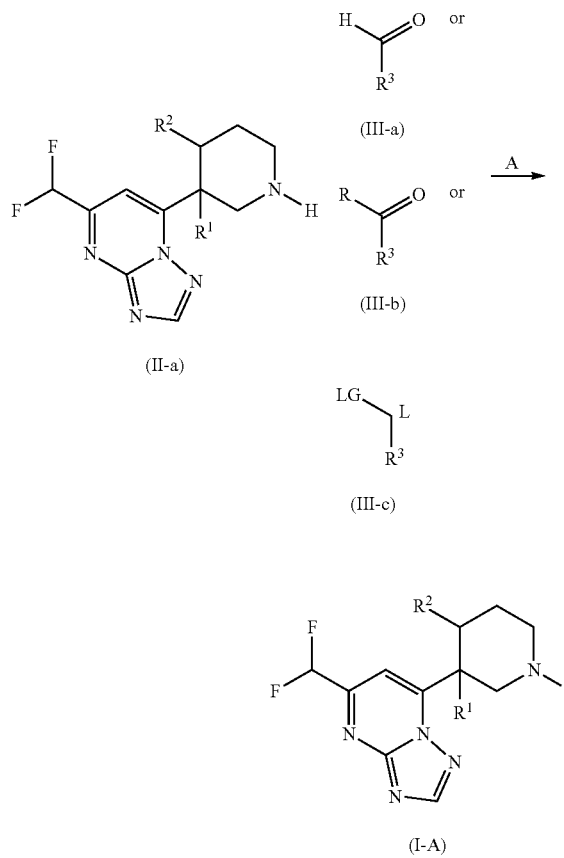

Reaction Scheme 1b

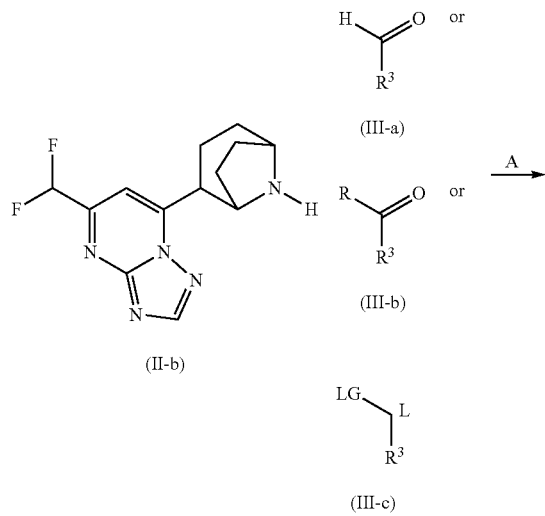

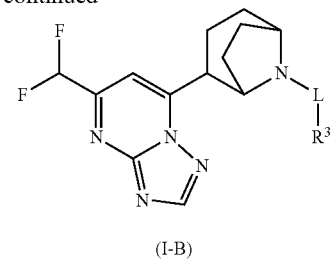

Final compounds wherein $R^B$ is a radical of Formula (a) or (b) herein referred to as compounds of Formula (I-A) and Formula (I-B), respectively, may be conveniently prepared by reaction with an appropriate aldehyde (III-a), ketone (III-b) (wherein R is $CH_3$ or $CF_3$) or substituted alkyl (III-c) following art-known coupling procedures (reaction step A). Said conversion may conveniently be conducted by treatment of the piperidine type functionality in the intermediates of Formula (II-a) or (II-b) with (III-a) followed by reaction with a reducing agent, such as sodium triacetoxyborohydride in the presence of a base, such as DIPEA and an appropriate solvent, such as DCM; with (III-b) in the presence of a catalyst such as $TiCl_4$, a base, such as triethylamine, in a suitable solvent, such as DCM, followed by reaction with a reducing agent, such as sodium cyanoborohydride in MeOH; or with (III-c), wherein LG is a leaving group, for instance a halogen or a mesylate, in the presence of a suitable base, such as triethylamine, in a suitable solvent, such as for example DMF. Reagents of Formula (III-a), (III-b) and (III-c) are either commercially available or can be prepared by art-known procedures.

Experimental Procedure 2

Reaction Scheme 2

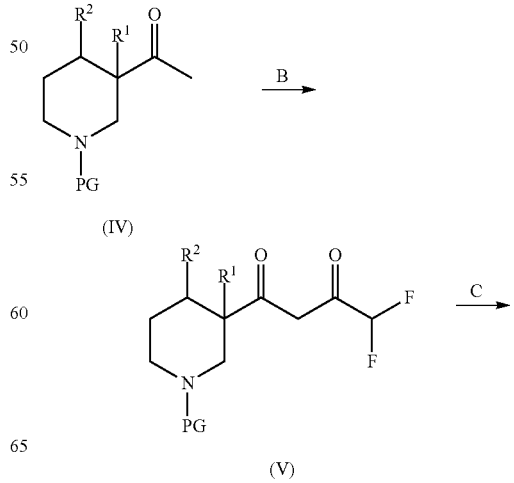

-continued

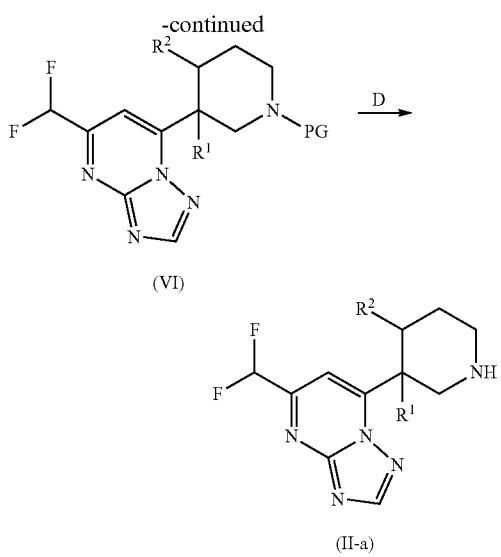

B: reaction with 2,2,-difluoro-acetic acid ethyl ester
C: reaction with 1H-1,2,4-triazol-3-amine hydrochloride
D: protecting group cleavage Formation of intermediates of Formula (II-a) can be prepared from intermediates of Formula (IV), wherein PG is a suitable amino protecting group, such as for example, tert-butyloxycarbonyl (Boc).

The reaction with 2,2-difluoroacetic acid ethyl ester can be performed in the presence of a base, such as KO$^t$Bu, in a reaction-inert solvent, such as toluene, at an appropriate temperature, such as 0-5° C., then at RT.

The bicyclic core can be formed by reaction of intermediate (V) with 1H-1,2,4-triazol-3-amine hydrochloride in a reaction-inert solvent, such as for example DMF, under thermal conditions, such as for example, heating at 80° C.

The cleavage of the protecting group in intermediate (VI) can be performed according to art-known procedures, for instance, when the protecting group is Boc, the cleavage can be performed under acidic conditions, such as for example HCl in MeOH at RT, or TFA in DCM.

Experimental Procedure 3

Reaction Scheme 3

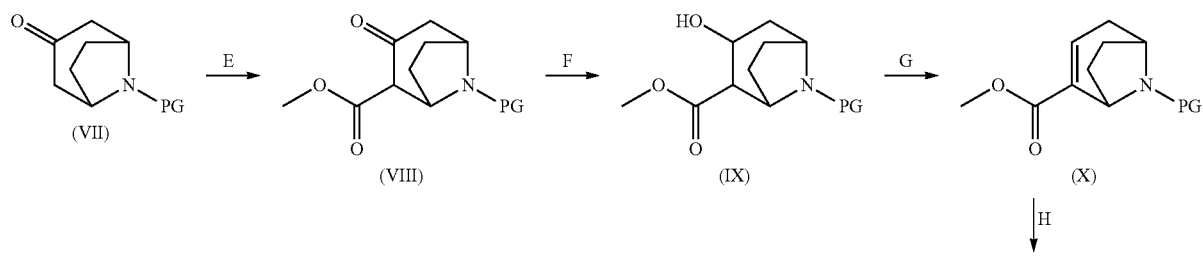

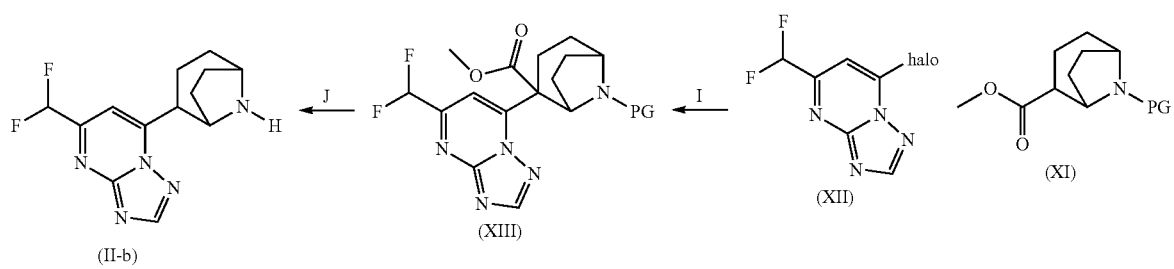

E: reaction with methyl cyanoformate
F: reduction
G: dehydration
H: hydrogenation
I: coupling
J: decarboxylation and protecting group cleavage Formation of intermediates of Formula (II-b) can be prepared by a series of synthetic steps starting from commercially available starting material of Formula (XIV), such as N-Boc-nortropinone [185099-67-6]. Reaction with methyl cyanoformate in the presence of a base such as nBuLi and NH$^i$Pr$_2$ in a reaction-inert solvent, such as THF at an appropriate temperature, such as at −78° C., affords keto-ester (VIII), which then can be reduced under art-known conditions with NaBH$_4$, for example in MeOH at about 0° C. and subsequently dehydrated with for example, trifluoroacetic anhydride in the presence of a base such as triethylamine and DMAP in a reaction inert solvent such as DCM, keeping the temperature below 60° C. Hydrogenation under art-known conditions, such as for example in the presence of palladium on carbon catalyst in MeOH affords intermediate (XI), which can then be reacted with intermediates of Formula (XII) which are either commercially available or made according to art-known procedures, in the presence of a base such as for example LDA, in a reaction-inert solvent, such as THF at a temperature between −78 to −60° C. Reaction with concentrated HCl under thermal conditions, such as for example, heating at 150° C. renders intermediate (II-b) with concomitant cleavage of the protecting group, when acid labile, such as for example, Boc.

Experimental Procedure 4

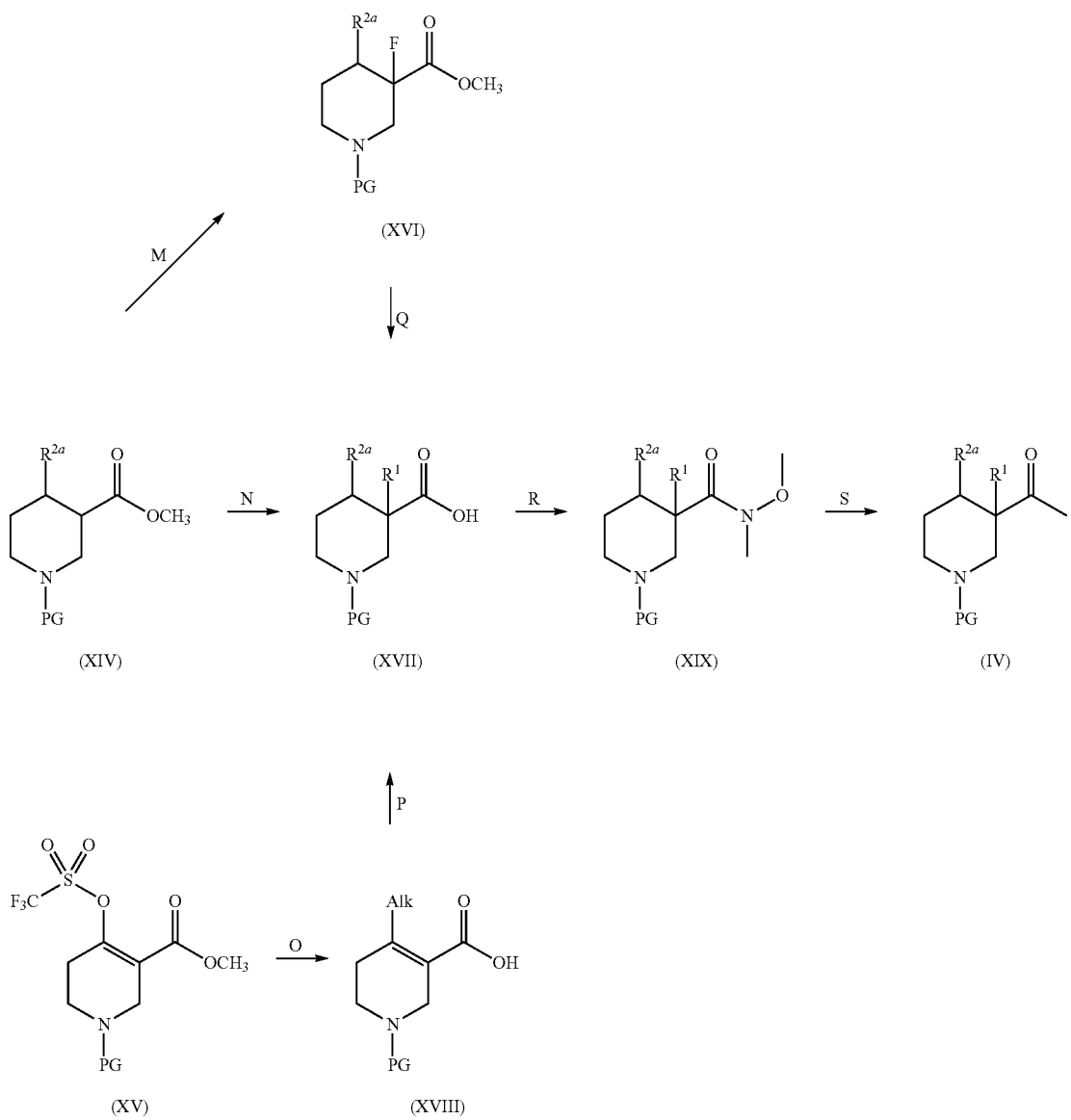

M: fluorination
N: methylation and/or saponification
O: Suzuki (alkylation) and saponification
P: hydrogenation
Q: saponification
R: Weinreb amide formation
S: amide to ketone conversion (Grignard)

The formation of intermediate (IV) can be performed by a series of functional group interconversions, starting from intermediates (XIV), (XV) or (XVI) which are either commercially available, or can be prepared for example, according to procedures such as those described herein.

Compounds of Formula (XIV), wherein $R^{2a}$ is hydrogen or methyl, and PG is Boc are either commercially available or made according to a series of known procedures, such as those described herein. They can be fluorinated or alkylated according to art-known procedures, such as by reaction with N-fluorobenzensulfonimide in the presence of a base such as LDA in a reaction-inert solvent such as THF, or by alkylation with alkyl iodide after treatment with a base such as LiHMDS; subsequent saponification under conditions known in the art, afford (XVII).

Compounds of Formula (XV) are also known in the art, can be alkylated, by means of Suzuki-type procedures, using conditions known to the skilled person, such as the use of a boronic acid/ester, in the presence of a catalyst, such as Pd(PPh$_3$)$_4$, in a reaction-inert solvent, such as 1,4-dioxane, under thermal conditions, such as heating. Subsequent saponification and hydrogenation under conditions analogous to those described herein, yield intermediate of Formula (XVII).

Subsequent Weinreb amide formation and amide to ketone conversion with Grignard), as described herein, afford the desired intermediate (IV).

Pharmacology

The compounds according to the invention inhibit PDE2 enzyme activity, in particular PDE2A, and hence raise the levels of cAMP or cGMP within cells that express PDE2. Accordingly, inhibition of PDE2 enzyme activity may be useful in the treatment of diseases caused by deficient amounts of cAMP or cGMP in cells. PDE2 inhibitors may also be of benefit in cases in which raising the amount of cAMP or cGMP above normal levels results in a therapeutic effect. Inhibitors of PDE2 may be used to treat neurological and psychiatric disorders.

Hence, the present invention relates to a compound of Formula (I) or a pharmaceutically acceptable salt or a solvate thereof according to the present invention, for use as a medicine, as well as to the use of a compound of Formula (I) or a pharmaceutically acceptable salt or a solvate thereof according to the invention or a pharmaceutical composition according to the invention for the manufacture of a medicament. The present invention also relates to a compound of Formula (I) or a pharmaceutically acceptable salt or a solvate thereof according to the present invention or a pharmaceutical composition according to the invention for use in the treatment or prevention of, in particular treatment of, a condition in a mammal, including a human, the treatment or prevention of which is affected or facilitated by the inhibition of phosphodiesterase 2 enzyme. The present invention also relates to the use of a compound of Formula (I) or a pharmaceutically acceptable salt or a solvate thereof according to the present invention or a pharmaceutical composition according to the invention for the manufacture of a medicament for the treatment or prevention of, in particular treatment of, a condition in a mammal, including a human, the treatment or prevention of which is affected or facilitated by the inhibition of phosphodiesterase 2 enzyme.

The present invention also relates to a compound of Formula (I) or a pharmaceutically acceptable salt or a solvate thereof according to the invention, or a pharmaceutical composition according to the invention for use in the treatment, prevention, amelioration, control or reduction of the risk of various neurological and psychiatric disorders associated with phosphodiesterase 2 dysfunction in a mammal, including a human, the treatment or prevention of which is affected or facilitated by the inhibition of phosphodiesterase 2.

Also, the present invention relates to the use of a compound of Formula (I) or a pharmaceutically acceptable salt or a solvate thereof according to the invention or a pharmaceutical composition according to the invention for the manufacture of a medicament for treating, preventing, ameliorating, controlling or reducing the risk of various neurological and psychiatric disorders associated with phosphodiesterase 2 dysfunction in a mammal, including a human, the treatment or prevention of which is affected or facilitated by the inhibition of phosphodiesterase 2.

Where the invention is said to relate to the use of a compound of Formula (I) or a pharmaceutically acceptable salt or a solvate thereof or composition according to the invention for the manufacture of a medicament for e.g. the treatment of a subject, e.g. a mammal, it is understood that such use is to be interpreted in certain jurisdictions as a method of e.g. treatment of a subject, comprising administering to a subject in need of such e.g. treatment, an effective amount of a compound of Formula (I) or a pharmaceutically acceptable salt or a solvate thereof or composition according to the invention.

In particular, the indications that may be treated with PDE2 inhibitors, either alone or in combination with other drugs, include, but are not limited to, those diseases thought to be mediated in part by the basal ganglia, prefrontal cortex and hippocampus.

These indications include neurological and psychiatric disorders selected from psychotic disorders and conditions; anxiety disorders; movement disorders; drug abuse; mood disorders; neurodegenerative disorders; disorders or conditions comprising as a symptom a deficiency in attention and/or cognition; disorders related to memory acquisition and consolidation; stroke; and autistic disorder or autism.

In particular, the psychotic disorders and conditions associated with PDE2 dysfunction include one or more of the following conditions or diseases: schizophrenia, for example of the paranoid, disorganized, catatonic, undifferentiated or residual type; schizophreniform disorder; schizoaffective disorder, such as delusional or depressive type; delusional disorder; substance-induced psychotic disorder such as psychosis induced by alcohol, amphetamine, cannabis, cocaine, hallucinogens, inhalants, opioids, or phencyclidine; personality disorders of the paranoid type; and personality disorder of the schizoid type.

In particular, the anxiety disorders include panic disorder; agoraphobia; specific phobia; social phobia; obsessive-compulsive disorder; post-traumatic stress disorder; acute stress disorder; and generalized anxiety disorder.

In particular, movement disorders include Huntington's disease and dyskinesia; Parkinson's disease; restless leg syndrome and essential tremor. Additionally, Tourette's syndrome and other tic disorders can be included.

In particular, the central nervous system disorder is a substance-related disorder selected from the group of alcohol abuse; alcohol dependence; alcohol withdrawal; alcohol withdrawal delirium; alcohol-induced psychotic disorder; amphetamine dependence; amphetamine withdrawal; cocaine dependence; cocaine withdrawal; nicotine dependence; nicotine withdrawal; opioid dependence and opioid withdrawal.

In particular, mood disorders and mood episodes include depression, mania and bipolar disorders. Preferably, the mood disorder is selected from the group of bipolar disorders (I and II); cyclothymic disorder; depression; dysthymic disorder; major depressive disorder; treatment-resistant depression; and substance-induced mood disorder.

In particular, neurodegenerative disorders include Parkinson's disease; Huntington's disease; dementia such as for example Alzheimer's disease; multi-infarct dementia; AIDS-related dementia or fronto temporal dementia. The neurodegenerative disorder or condition comprises dysfunction of striatal medium spiny neurons responses.

In particular, disorders or conditions comprising as a symptom a deficiency in attention and/or cognition include dementia, such as Alzheimer's disease; multi-infarct dementia; dementia due to Lewy body disease; alcoholic dementia or substance-induced persisting dementia; dementia associated with intracranial tumours or cerebral trauma; dementia associated with Huntington's disease; dementia associated with Parkinson's disease; AIDS-related dementia; dementia due to Pick's disease; dementia due to Creutzfeldt-Jakob disease; other diseases include delirium; amnestic disorder; post-traumatic stress disorder; stroke; progressive supranuclear palsy; mental retardation; a learning disorder; attention-deficit/hyperactivity disorder (ADHD); mild cognitive disorder; Asperger's syndrome; age-related cognitive impairment; and cognitive impairment related to perception, concentration, learning or memory.

In particular, disorders related to memory acquisition and consolidation include, memory disorders, such as age-associated memory losses, memory deficiency.

Preferably, the psychotic disorder is selected from the group of schizophrenia, delusional disorder, schizoaffective disorder, schizophreniform disorder and substance-induced psychotic disorder.

Preferably, the central nervous system disorder is a personality disorder selected from the group of obsessive-compulsive personality disorder and schizoid, schizotypal disorder.

Preferably, the central nervous system disorder is a mood disorder selected from the group of bipolar disorders (I & II), cyclothymic disorder, depression, dysthymic disorder, major depressive disorder; treatment-resistant depression; and substance-induced mood disorder.

Preferably, the central nervous system disorder is attention-deficit/hyperactivity disorder.

Preferably, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

Preferably the disorders treated by the compounds of formula (I) or a pharmaceutically acceptable salt or a solvate thereof of the present invention are selected from schizophrenia; obsessive-compulsive disorder; generalized anxiety disorder; Huntington's disease; dyskinesia; Parkinson's disease; depression; bipolar disorders; dementia such as Alzheimer's disease; attention-deficit/hyperactivity disorder; drug abuse; stroke; and autism.

Preferably, the disorders treated by the compounds of formula (I) or a pharmaceutically acceptable salt or a solvate thereof of the present invention are schizophrenia, including positive and negative symptoms thereof, and cognitive deficits, such as impaired attention or memory.

Of the disorders mentioned above, the treatment of anxiety, obsessive-compulsive disorder, post-traumatic stress disorder; generalized anxiety disorder, schizophrenia, depression, attention-deficit/hyperactivity disorder, Alzheimer's disease, dementia due to Huntington's disease, dementia due to Parkinson's disease, dementia of the Alzheimer's type, substance-induced persisting dementia and mild cognitive impairment are of particular importance.

Of the disorders mentioned above, the treatment of anxiety, obsessive-compulsive disorder, schizophrenia, depression, attention-deficit/hyperactivity disorder, and Alzheimer's disease are of particular importance.

Other central nervous system disorders include schizo-anxiety disorder, and comorbid depression and anxiety, in particular major depressive disorder with comorbid generalized anxiety disorder, social anxiety disorder, or panic disorder; it is understood that comorbid depression and anxiety may also be referred to by the terms anxious depression, mixed anxiety depression, mixed anxiety-depressive disorder, or major depressive disorder with anxiety symptoms, which are used indistinctively herein.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses. For example, the "American Psychiatric Association: Diagnostic and Statistical Manual of Mental Disorders, Fifth Edition. Arlington, Va., American Psychiatric Association, 2013" (DSM-5™) utilizes terms such as depressive disorders, in particular, major depressive disorder, persistent depressive disorder (dysthymia), substance-medication-induced depressive disorder; neurocognitive disorders (NCDs) (both major and mild), in particular, neurocognitive disorders due to Alzheimer's disease, vascular NCD (such as vascular NCD present with multiple infarctions), NCD due to HIV infection, NCD due to traumatic brain injury (TBI), NCD due to Parkinson's disease, NCD due to Huntington's disease, frontotemporal NCD, NCD due to prion disease, and substance/medication-induced NCD; neurodevelopmental disorders, in particular, intellectual disability, specific learning disorder, neurodevelopmental motor disorder, communication disorder, and attention-deficit/hyperactivity disorder (ADHD); substance-related disorders and addictive disorders, in particular, alcohol use disorder, amphetamine use disorder, cannabis use disorder, cocaine use disorder, other hallucinogen use disorder, tobacco use disorder, opioid use disorder, and phencyclidine use disorder; schizophrenia spectrum and other psychotic disorders, in particular, schizophrenia, schizophreniform disorder, schizoaffective disorder, delusional disorder, brief psychotic disorder, substance/medication-induced psychotic disorder; and cyclothymic disorder (which under DSM-5™ falls under the bipolar and related disorders category). Such terms may be used by the skilled person as an alternative nomenclature for some of the diseases or conditions referred to herein. An additional neurodevelopmental disorder includes autism spectrum disorder (ASD), which encompasses according to the DSM-5™, disorders previously known by the terms early infantile autism, childhood autism, Kanner's autism, high-functioning autism, atypical autism, pervasive developmental disorder not otherwise specified, childhood disintegrative disorder, and Asperger's disorder.

Therefore, the invention also relates to a compound of Formula (I) or a pharmaceutically acceptable salt or a solvate thereof according to the invention, for use in the treatment of any one of the diseases mentioned hereinbefore.

The invention also relates to a compound of Formula (I) or a pharmaceutically acceptable salt or a solvate thereof according to the invention for use in treating any one of the diseases mentioned hereinbefore.

The invention also relates to a compound of Formula (I) or a pharmaceutically acceptable salt or a solvate thereof according to the invention, for the treatment or prevention, in particular treatment, of any one of the diseases mentioned hereinbefore.

The invention also relates to the use of a compound of Formula (I) or a pharmaceutically acceptable salt or a solvate thereof according to the invention, for the manufacture of a medicament for the treatment or prevention of any one of the disease conditions mentioned hereinbefore.

The invention also relates to the use of a compound of Formula (I) or a pharmaceutically acceptable salt or a solvate thereof according to the invention for the manufacture of a medicament for the treatment of any one of the disease conditions mentioned hereinbefore.

The compound of Formula (I) or a pharmaceutically acceptable salt or a solvate thereof of the present invention can be administered to mammals, preferably humans, for the treatment or prevention of any one of the diseases mentioned hereinbefore.

In view of the utility of the compounds of Formula (I), and the pharmaceutically acceptable salts and the solvates thereof, according to the invention, there is provided a method of treating a disorder or disease mentioned hereinbefore, comprising administering to a subject in need thereof, a therapeutically effective amount of a compound of Formula (I) or a pharmaceutically acceptable salt or a solvate thereof or pharmaceutical compositions described herein.

Said methods comprise the administration, i.e. the systemic or topical administration, preferably oral administration, of a therapeutically effective amount of a compound of Formula (I) or a pharmaceutically acceptable salt or a solvate thereof according to the invention to warm-blooded animals, including humans.

Therefore, the invention also relates to a method for the prevention and/or treatment of any one of the diseases mentioned hereinbefore comprising administering a therapeutically effective amount of a compound of Formula (I) or a pharmaceutically acceptable salt or a solvate thereof according to the invention to a patient in need thereof.

The PDE2 inhibitor described herein can be used alone, in combination or in combination with other pharmaceutical agents such as other agents used in the treatment of psychoses, such as schizophrenia and bipolar disorder, obsessive-compulsive disorder, Parkinson's disease, cognitive impairment and/or memory loss, e.g. nicotinic α-7 agonists, PDE4 inhibitors (Rolipram, GEBR-7b, GSK356278, GSK256066, Apremilast, MK-0952, Roflumilast, AN2898, AN2728, Ariflo Cilomilast, Dotraverine, Ronomilast Elbimilast, Revamilast, Tetomilast, E6005, GDP-1116, HT0712, MK-0873), PDE5 inhibitors (Sildenafil, Vardenafil, Tadalafil, Udenafil, Avanafil, Mirodenafil, Lodenafil, Dasantafil, PF-00489791), PDE9 (PF-04447943), other PDE2 inhibitors (Bay 60-7550, PF-999, ND-7001), PDE10 inhibitors (PF-02545920, AMG579), PDE2 and 10 inhibitors, calcium channel blockers, muscarinic m1 and m2 modulators, adenosine receptor modulators, ampakines, NMDA-R modulators, mGluR modulators, dopamine modulators, serotonin modulators, cannabinoid modulators, HDAC inhibitors (Vorinostat SAHA, Panobinostat, Quisinostat, Valproic acid) and cholinesterase inhibitors (e.g. donepezil, rivastigmine, and galantamine). In such combinations, the compound of Formula (I) or a pharmaceutically acceptable salt or a solvate thereof of the present invention may be utilized in combination with one or more other drugs in the treatment, prevention, control, amelioration, or reduction of risk of diseases or conditions for which the compound of Formula (I) or the other drugs may have utility, where the combination of the drugs together are safer or more effective than either drug alone.

One skilled in the art will recognize that a therapeutically effective amount of the PDE2 inhibitor of the present invention is the amount sufficient to inhibit the PDE2 enzyme and that this amount varies inter alia, depending on the type of disease, the concentration of the compound in the therapeutic formulation, and the condition of the patient. Generally, an amount of PDE2 inhibitor to be administered as a therapeutic agent for treating diseases in which inhibition of the PDE2 enzyme is beneficial, such as the disorders described herein, will be determined on a case by case by an attending physician.

Generally, a suitable dose is one that results in a concentration of the PDE2 inhibitor at the treatment site in the range of 0.5 nM to 200 µM, and more usually 5 nM to 50 µM. To obtain these treatment concentrations, a patient in need of treatment likely will be administered between 0.001 mg/kg to 15 mg/kg body weight, in particular from 0.01 mg/kg to 2.50 mg/kg body weight, in particular, from 0.01 to 1.5 mg/kg body weight, in particular from 0.1 mg/kg to 0.50 mg/kg body weight. The amount of a compound according to the present invention, also referred to here as the active ingredient, which is required to achieve a therapeutical effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compound according to the invention is preferably formulated prior to admission. As described herein below, suitable pharmaceutical formulations are prepared by known procedures using well known and readily available ingredients.

Pharmaceutical Compositions

The present invention also provides compositions for preventing or treating diseases in which inhibition of PDE2 is beneficial, such as neurological and psychiatric disorders. Said compositions comprising a therapeutically effective amount of a compound of Formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy. A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The present compound can be used for systemic administration such as oral, percutaneous or parenteral administration; or topical administration such as via inhalation, a nose spray, eye drops or via a cream, gel, shampoo or the like. The compound is preferably orally administered.

The exact dosage and frequency of administration depends on the compound, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compound of the instant invention.

The amount of the compound of Formula (I) that can be combined with a carrier material to produce a single dosage form will vary depending upon the disease treated, the mammalian species, and the particular mode of administration. However, as a general guide, suitable unit doses for the compound of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

For the compositions, methods and kits provided above, one of skill in the art will understand that the preferred compound for use in each is the compound noted herein

EXPERIMENTAL PART

As used herein, the term "ACN" means acetonitrile, "AcOH" means acetic acid, "DMAP" 4-dimethylaminopyridine, "DSC" means differential scanning calorimetry, "LCMS" means liquid chromatography/mass spectrometry, "HPLC" means high-performance liquid chromatography, "RP HPLC" means reverse phase high-performance liquid chromatography, "aq." means aqueous, "DCM" means dichloromethane, "DIPE" means diisopropyl ether, "DIPEA" means diisopropylethyl amine, "DMF" means N,N-dimethylformamide, "EtOH" means ethanol, "Et$_2$O" means diethylether, "EtOAc" means ethyl acetate, "Et$_3$N" means triethylamine, "HBTU" means O-(benzotriazol-1-yl)-N,N,N'N,'-tetramethyluroniumhexafluoro-phosphate, "THF" means tetrahydrofuran, "min" means minutes, "h" means hours, "MeOH" means methanol, "MTBE" means methyl tert-butyl ether, "iPrOH" means 2-propanol, "RM" means reaction mixture, "RT" means room temperature, "OL" means organic layer, "Rt" means retention time (in minutes), "quant." means quantitative, "sat." means saturated, "sol." means solution, "m.p." means melting point, "q.s." means quantum sufficit.

Thin layer chromatography (TLC) was carried out on silica gel 60 F254 plates (Merck) using reagent grade solvents. Open column chromatography was performed on silica gel, mesh 230-400 particle size and 60 Å pore size (Merck) under standard techniques.

Automated flash column chromatography was performed using ready-to-connect cartridges from Merck, on irregular silica gel, particle size 15-40 μm (normal phase disposable flash columns) on an SPOT or LAFLASH system from Armen Instrument.

When a stereocenter is indicated with 'RS' this means that a racemic mixture was obtained at the indicated centre, unless otherwise indicated. The stereochemical configuration for centres in some compounds may be designated "R" or "S" when the mixture(s) was separated; for some compounds, the stereochemical configuration at indicated centres has been designated as "*R" or "*S" when the absolute stereochemistry is undetermined although the compound itself has been isolated as a single stereoisomer and is enantiomerically/diastereomerically pure.

The absolute stereochemical configuration for some of the compounds was determined using vibrational circular dichroism (VCD). They were measured on a Bruker Equinox 55 equipped with a PMA 37, in a KBr liquid cell using $CD_2Cl_2$ as solvent (PEM: 1350 cm-1, LIA: 1 mV, resolution: 4 $cm^{-1}$). A description on the use of VCD for the determination of absolute configuration can be found in Dyatkin A. B. et. al, Chirality, 14:215-219 (2002). Ab initio calculations: A thorough conformational search was performed at molecular mechanics level using Macromodel to do a mixed torsional/low-mode sampling with the OPLS-2005 force field. The located minima were optimized using Jaguar on the B3LYP/6-31G level with a Poisson-Boltzmann continuum solvation model to mimic a dichloromethane solvent. All conformations within 10 kJ/mol interval were used to simulate VCD and IR spectrum. Dipole and rotational strengths were calculated at the same B3LYP/6-31G level, using Jaguar. The calculated VCD spectra, generated after scaling the frequencies with a factor of 0.97, converting to a Lorentzian bandshape, and summing up the contribution of each conformer assuming a Boltzmann ensemble, were visually compared with the experimental spectra for assigning the correct stereo chemistry.

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

The following examples are intended to illustrate but not to limit the scope of the present invention. Unless otherwise noted, all starting materials were obtained from commercial suppliers and used without further purification.

A. Synthesis of Intermediates

Intermediate 1

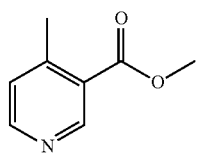

Procedure a: 4-Methyl-3-pyridinecarboxylic acid hydrochloride (1:1) (40 g, 230.4 mmol) was added to a refluxing mixture of sulphuric acid (20 mL) and MeOH (400 mL). The mixture was refluxed overnight, then it was evaporated and the resulting slurry was added to a cold solution of $NaHCO_3$ (64 g) in water (360 mL). The product was extracted with DCM and the OL was dried over $MgSO_4$, filtered and evaporated, yielding intermediate 1 (28.70 g, 83%).

Procedure b: A metal reactor was charged with 3-bromo-4-methyl-pyridine (200 g, 0.116 mol) and a mixture of DMF/MeOH (1 L/1 L). To this was added $Et_3N$ (400 g, 0.395 mol), palladium (II) acetate (8 g, 0.036 mol) and 1,1'-bis(diphenylphosphino)ferrocene (16 g, 0.029 mol). The reactor was closed and pressurized with CO gas (3 MPa) and the reaction mixture was stirred and heated overnight at 140° C. The RM was cooled, filtered and concentrated in vacuo. The residue was purified by flash column chromatography over silica gel (gradient eluent: EtOAc/Petroleum ether from 1/1 to 1/0). The product fractions were collected and the solvent was evaporated to afford the desired intermediate 1 (90 g, 51%).

Intermediate 2

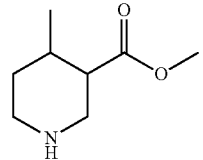

Procedure a: A hydrogenation flask was charged with AcOH (500 mL) and then $PtO_2$ (15.02 g, 66.2 mmol) was added. Intermediate 1 (50 g, 330.8 mmol) was added and the mixture was hydrogenated at 50° C. for 7 days. The RM was filtered over Dicalite® and the filtrate was evaporated to yield intermediate 2 (52 g), which was used in the next step without further purification.

Procedure b: Platinum oxide (5 g, 0.022 mol) was added to a solution of intermediate 1 (90 g, 0.595 mol) and AcOH (1 L). The r.m. was stirred and hydrogenated for 5 days at 50° C. under a pressure of 3.5 kPa. The cooled RM was concentrated in vacuo to give intermediate 2 as the acetic acid salt (140 g, 97%, 90% purity determined by $^1$H-NMR).

Intermediate 3

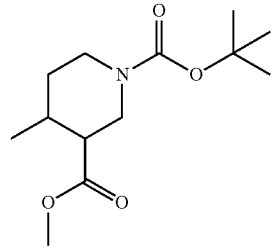 [SMILES: COC(=O)C1CN(C(=O)OC(C)(C)C)CCC1C]

Procedure a: To a solution of intermediate 2 (52 g, 330.8 mmol) in DCM (869 mL), DIPEA (85.5 g, 661.5 mmol) and DMAP (4.04 g, 33.08 mmol) were added. Then di-tert-butyl dicarbonate (72.19 g, 330.8 mmol) was added to this solution in small portions and the reaction was stirred at RT for 1 h. The RM was washed with water and brine and the organic layer was dried over MgSO$_4$, filtered and evaporated. The product was purified by column chromatograph (silica gel, eluent: DCM, 1% MeOH in DCM, 2%, 4%). The desired fractions were evaporated, yielding intermediate 3 (64.1 g, 75%).

Procedure b: To a stirred and cooled (0° C.) solution of intermediate 2 (140 g, 0.595 mol) in DCM (1.5 L) was added sequentially di-tert-butyl dicarbonate (130 g, 0.596 mol), Et$_3$N (225 g, 1.74 mol) and DMAP (10 g, 0.082 mol) and stirring was continued at RT for 2 h. The reaction mixture was poured onto H$_2$O (500 mL) and extracted with DCM (2×100 mL). The organic layers were separated, dried (Na$_2$SO$_4$), and the solvent was evaporated to give crude intermediate 3 (150 g, 90%, 90% purity determined by $^1$H-NMR) which was used as such in the next.

Intermediate 4

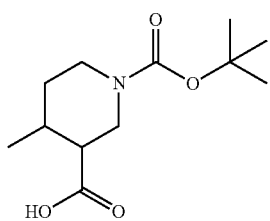 [SMILES: CC1CCN(C(=O)OC(C)(C)C)CC1C(=O)O]

Procedure a: Intermediate 3 (64.1 g, 249.1 mmol) was stirred in MeOH (500 mL) at RT. NaOH (2 M, 747.3 mL) was added and the mixture was stirred for 2 h at RT. The RM was acidified with HCl 1N and the product was extracted with Et$_2$O. The OL was washed with brine and dried over MgSO$_4$, filtered and evaporated, yielding intermediate 4 (59.70 g) as a white solid.

Procedure b: To a stirred solution of intermediate 3 (150 g, 90% pure, 0.524 mol) in MeOH (0.9 L) was added a solution of a 2M NaOH solution (1.8 mol). After 14 h at RT, the RM was extracted with MTBE (2×0.8 L). The aqueous layer was acidified with 10% citric acid and then extracted with EtOAc (4×1 L). The combined organic layers were dried over Na$_2$SO$_4$, filtered and concentrated in vacuo to give crude intermediate 4 (142 g, 90% purity determined by $^1$H-NMR, 100%) which was used as such in the next step.

Intermediate 5

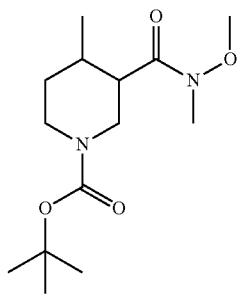

Procedure a: To a solution of intermediate 4 (59.7 g, 0.25 mol) in THF (800 mL), was added di-1H-imidazol-1-yl-methanone (54 g, 0.33 mol) and the mixture was stirred at RT for 1 h. In another flask, to a suspension of N-methoxy-methanamine hydrochloride (1:1) (32.93 g, 0.34 mol) in ACN (500 mL), was added trimethylamine (35.75 g, 0.35 mol). Both mixtures were combined and stirred at 50° C. while monitoring. The intermediate product crystallized out of the RM and did not react with N-methoxy-methanamine to form the desired product. DCM was added until the intermediate dissolved. The reaction was left stirring for 1 week at 80° C. The solvents were evaporated. The residue was dissolved in DCM and washed with water, 20% AcOH solution and finally with a saturated NaHCO$_3$ solution. The OL was dried over MgSO$_4$, filtered and evaporated. The product was purified by column chromatography (silica gel, eluent: 2% MeOH in DCM, 4%). The pure fractions were evaporated, yielding intermediate 5 (70 g, quantitative).

Procedure b: To a stirred and ice-cooled solution of intermediate 4 (140 g, 0.518 mol) in DCM (2 L) was added N,O-dimethylhydroxylamine (113 g, 1.16 mol) and Et$_3$N (113 g, 1.79 mol). Then HATU (235 g, 0.618 mol) was added and stirring was continued for 14 h. The solvent was evaporated and a NaHCO$_3$ solution (0.5 L) was added and then extracted with DCM (3×1 L). The combined organic layers were separated, dried over Na$_2$SO$_4$, filtered and concentrated in vacuo. The residue was purified by silica gel flash chromatography eluting with 1-10% EtOAc in petroleum ether to afford intermediate 5 (152 g, 100%).

Intermediate 6

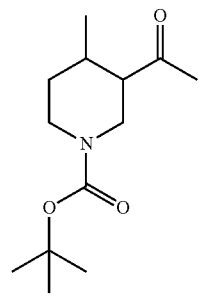 [SMILES: CC(=O)C1CN(C(=O)OC(C)(C)C)CCC1C]

Procedure a: Intermediate 5 (70 g, 244.4 mmol) in THF (250 mL) was charged in a flask under N$_2$ and cooled to −15° C. Methylmagnesium bromide (1.4 M in toluene/THF 75/25, 206 mL) was added dropwise, with the temperature not exceeding 0° C. After addition, the RM was stirred at RT for 1 h. Then the RM was poured on ice with 20 mL AcOH. The product was extracted with Et$_2$O and the OL was washed with a 5% NaHCO$_3$ solution. The OL was dried over MgSO$_4$, filtered and evaporated to give intermediate 6 (53.35 g, 90%).

Procedure b: To a stirred and cooled solution (0° C.) of intermediate 5 (150 g, 0.524 mol) in THF (2 L) was added dropwise a 3M methylmagnesium bromide solution in THF (0.75 L, 2.25 mol) and stirring was continued at RT for 2 h. The reaction mixture was poured onto aqueous NH$_4$Cl solution and extracted with DCM. The combined organic layers were dried over Na$_2$SO$_4$, filtered and concentrated in vacuo. The residue was purified by silica gel chromatography eluting with 1-5% EtOAc in petroleum ether to afford intermediate 6 (120 g, 95%).

Intermediate 7

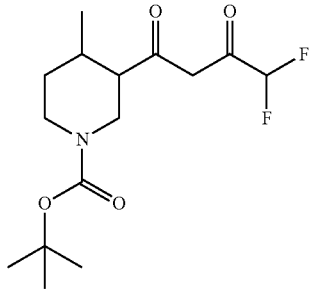 [SMILES: CC1CCN(C(=O)OC(C)(C)C)CC1C(=O)CC(=O)C(F)F]

Intermediate 6 (53.35 g, 0.22 mol) was stirred in toluene (1500 mL) at 0° C. under $N_2$. Potassium tert-butoxide (34.14 g) was added at 0-5° C. and 2,2-difluoro-acetic acid ethyl ester (33.01 g, 0.27 mol) was added dropwise at 0-5° C. The RM was stirred at RT for 2 h, then washed with 10% $H_2SO_4$ in water and the OL was dried on $MgSO_4$, filtered and evaporated, yielding intermediate 7 (70.50 g, quantitative).

Intermediate 8

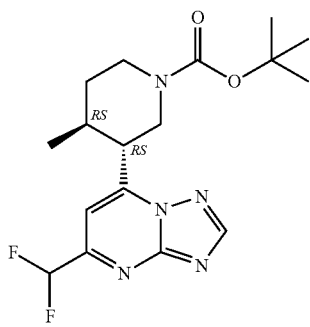 [SMILES: C[C@H]1CCN(C(=O)OC(C)(C)C)C[C@@H]1c1cc(C(F)F)nc2ncnn12]

Intermediate 7 (70.5 g, 220.8 mmol), 1H-1,2,4-triazol-5-amine hydrochloride (1:1) (53.22 g, 441.52 mmol) and DMF (1500 mL) were stirred at 80° C. for 24 h. $Et_3N$ (20 g) and di-tert-butyl dicarbonate (20 g) were added. The mixture was stirred for 30 min, evaporated and then dissolved in EtOAc, washed with water and brine. The OL was dried over $MgSO_4$, filtered and evaporated. Four isomers were observed. The first fraction crystallized from $Et_2O$. The crystals were filtered off and dried, yielding intermediate 8 (24.60 g, 30%). The mother liquor yielded a second fraction of the compound. The crystals were filtered off and dried, yielding intermediate 8 (2.53 g, 3%). N.B. "RS" means the intermediate is a racemic mixture of two enantiomers of trans relative configuration.

Intermediates 9, 9A and 9B

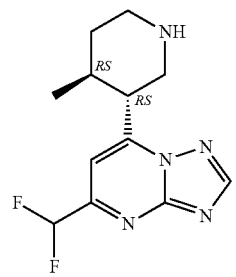

Intermediate 9

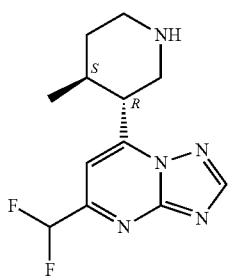

Intermediate 9a

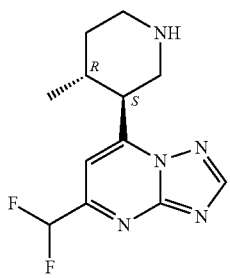

Intermediate 9b

To a solution of intermediate 8 (24.6 g, 67 mmol) in MeOH (350 mL), was added HCl-iPrOH (350 mL) and the RM was stirred for 2 h at RT. The RM was evaporated and the product was crystallized from EtOH. The crystals were filtered off and dried, yielding 20.33 g of a crude, to which water, $Na_2CO_3$ and DCM were added. The OL was dried over $MgSO_4$, filtered and evaporated, yielding 12.80 g of intermediate 9. This free base was separated into enantiomers 9a and 9b by purification by Prep SFC (Stationary phase: Chiralpak Diacel AD 30×250 mm; mobile phase: $CO_2$, ((MeOH-iPrOH 50/50) with 0.4% $iPrNH_2$), yielding intermediate 9a (5 g, 19%, Rt=7.57 min) and intermediate 9b (5.13 g, 19%, Rt=9.36 min).

Intermediates 9a and 9b were isolated as free bases or alternatively, they were dissolved in MeOH, followed by addition of HCl/i-PrOH and the mixture evaporated. The hydrochloride salts (in each instance, .HCl) were crystallized from ACN, filtered off and dried.

Intermediate 10

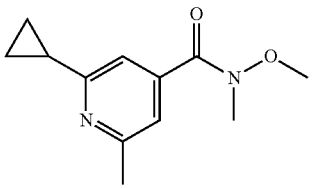 [SMILES: CON(C)C(=O)c1cc(C)nc(C2CC2)c1]

CDI [530-62-1] (2.96 g, 18.25 mmol) was added at r.t. to a solution of 2-cyclopropyl-6-methyl-4-pyridinecarboxylic acid [1256805-64-7] in DCM [75-09-2] (50 mL, 1.326 g/mL) and the r.m. was stirred at r.t. for 30 min. N,O-dimethylhydroxyl amine hydrochloric salt (1.92 g, 19.66 mmol) was then added and the r.m. stirred at r.t. until completion. The r.m. was diluted with DCM and washed with water and brine. The organic layer was dried on MgSO$_4$, filtered and evaporated in vacuo to give intermediate 10 (2.67 g, yield 86.33%), pure enough to be used as such in the next steps.

Intermediate 11

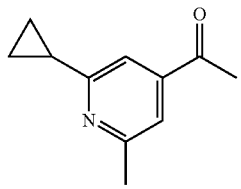

Intermediate 10 (1.05 g, 3.495 mmol) was dissolved in anhydrous THF (30 mL) and cooled to −15° C. under a N$_2$ atmosphere. A solution of methylmagnesium bromide in toluene/THF (75/25) (8.77 mL, 1.4 M, 12.28 mmol) was added dropwise, keeping the temperature of the reaction during the addition below 0° C. The r.m. was then stirred at r.t. for 1 hour, then it was cooled to −10° C. (iPrOH/ice bath) and treated with an aq. satd. NH$_4$Cl (20 mL) solution, maintaining temperature below 5° C. The aqueous layer was extracted thrice with EtOAc, then the combined organic layers were washed with brine, dried over MgSO$_4$, filtered and evaporated to give intermediate 11 (757 mg, yield 90.626%), of sufficient purity to be used as such in the next step.

Intermediate 12

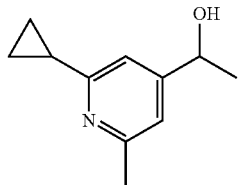

Intermediate 11 (410 mg, 2.34 mmol) was dissolved in MeOH (15 mL). NaBH$_4$ [16940-66-2] (89 mg, 2.34 mmol) was added at RT and the RM stirred for 15 min. Aq. sat. NaHCO$_3$ sol. was added, stirred 10 min, then the aqueous layer extracted three times with DCM. The combined organic layers were washed once with brine, then dried (MgSO$_4$), filtered and evaporated to give intermediate 12 (364 mg, yield 87.8%), of sufficient purity to be used as such in the next step.

Intermediate 13

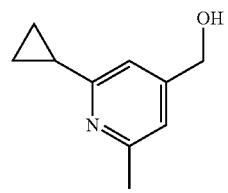

Di-isobutyl aluminium hydride (DIBAH) [1191-15-7] (2.27 mL, 1.2 M, 2.72 mmol) was added to a solution of intermediate 10 (500 mg, 2.27 mmol) in THF [109-99-9] (20.96 mL) at −78° C. under an atmosphere of N$_2$. The mixture was stirred at −78° C. for 10 min then warmed to RT and stirred for 2 h. The reaction was poured into 1N HCl and extracted with EtOAc (3×). The combined OL was washed with water and brine, dried over MgSO$_4$, filtered and concentrated in vacuo. The resulting residue was dissolved in MeOH [67-56-1] (15 mL), treated with sodium borohydride [16940-66-2] (100 mg, 2.643 mmol) and stirred at RT for 1 h and 30 min. The RM was quenched with a saturated aqueous NaHCO$_3$ solution, extracted with EtOAc (3×). The combined org layers were dried over MgSO$_4$, filtered and evaporated in vacuo, to give intermediate 13 (293 mg, yield 79%), which was pure enough to be used as such in the next step.

Intermediate 14

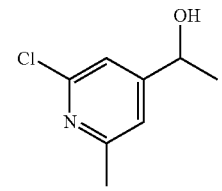

By following a procedure similar to the one reported for the synthesis of intermediate 12 ( ), starting from 1-(2-chloro-6-methyl-4-pyridinyl)-ethanone [890406-52-7] (620 mg, 3.655 mmol) intermediate 14 was obtained (600 mg, yield 95.64%).

Intermediate 15

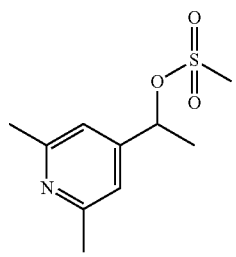

4-Pyridinemethanol [1702281-97-7] (300 mg, 1.98 mmol) was dissolved in anhydrous DCM [75-09-2] (5.52 mL, 1.326 g/mL, 86.13 mmol). The resulting solution was cooled to 0° C. Et$_3$N [121-44-8] (552 µL, 0.728 g/mL, 3.97 mmol) was added, followed by MsCl [124-63-0] (231 µL, 1.474 g/mL, 2.98 mmol) and the r.m. was stirred at 0° C. until completion. Aq. sat. NaHCO$_3$ sol. was added and the organic layer was separated, dried on MgSO$_4$, filtered and evaporated in vacuo, to give 500 mg of intermediate 15 as a crude, which was used as such in the next step.

Intermediate 16

Step 1. Intermediate 17

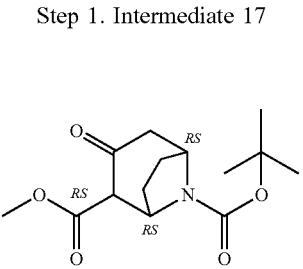

n-Butyllithium (nBuLi, 106.5 mL, 266.3 mmol, 2.5 M in hexanes) was added at 0° C. to a solution of diisopropylamine (26.95 g, 266.3 mmol) in THF (500 mL). The reaction mixture was stirred at 0° C. for 30 min, then it was cooled to −78° C. and treated with a solution of N-Boc-nortropinone (50 g, 221.9 mmol) in THF (75 mL). The resulting mixture was stirred at −78° C. for 90 min, then methyl cyanoformate (22.9 mL, 288.5 mmol) was added. The RM was allowed to warm to RT and stirred overnight. The reaction mixture was quenched with a saturated aqueous NH$_4$Cl solution, then it was diluted with EtOAc. The organic layer was separated, then washed with water and brine, dried over MgSO$_4$, filtered and concentrated under reduced pressure. The resulting residue was purified by flash column chromatography on silica gel using as eluent a gradient: 100% DCM to 1% MeOH in DCM, to provide intermediate 17 (60.25 g, 95.8%).

Step 2. Intermediate 18

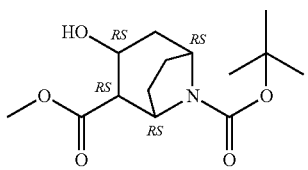 [SMILES: COC(=O)C1C(O)CC2CCC1N2C(=O)OC(C)(C)C]

Sodium borohydride (16.02 g, 423.5 mmol) was added to a cold (ice-bath) solution of intermediate 17 (60 g, 211.8 mmol) in methanol (700 mL) and the reaction mixture allowed to stir for 5 h. The completed reaction was quenched with a saturated aqueous NH$_4$Cl solution, then the solvent was evaporated to dryness under reduced pressure. The resulting residue was dissolved in water and extracted 3×DCM. The combined organic layers were dried over MgSO$_4$, filtered and concentrated in vacuo, to afford intermediate 18 (59 g, 97.6%) which was used as such without further purification.

Step 3. Intermediate 19

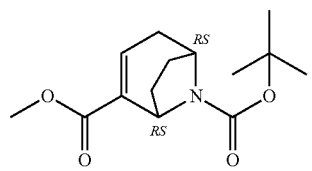 [SMILES: COC(=O)C1=CCC2CCC1N2C(=O)OC(C)(C)C]

Trifluoroacetic anhydride (57.5 mL, 413.5 mmol) was added dropwise very slowly (CAUTION! Exothermic) to a solution of intermediate 18 (59 g, 206.8 mmol), triethylamine (115 mL, 827.1 mmol) and 4-(dimethylamino) pyridine (2.52 g, 20.7 mmol) in DCM (800 mL), while keeping the temperature below 60° C. The reaction mixture was stirred at RT overnight, then it was cooled in an ice bath and quenched with water. The pH of the resulting solution was adjusted to 8-8.5 using a saturated aqueous NaHCO$_3$ solution and allowed to stir at RT for 1 hour. The aqueous was then extracted 3×DCM, then the combined organic layers were dried over MgSO$_4$, filtered and concentrated in vacuo. The resulting residue was purified by flash column chromatography on silica gel, using as eluent a gradient 100% DCM to 2% MeOH in DCM, to afford intermediate 19 (33.7 g, 61%).

Step 4. Intermediate 20

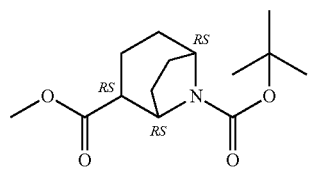 [SMILES: COC(=O)C1CCC2CCC1N2C(=O)OC(C)(C)C]

MeOH (59 mL) was added to a flask containing intermediate 19 (2.44 g, 9.13 mmol) and Pd/C (10%) (0.971 g, 0.913 mmol) under a nitrogen atmosphere. This was evacuated and backfilled with hydrogen gas and stirred at RT overnight. The reaction mixture was filtered over a pad of Celite®, then the solvent was removed in vacuo. The resulting residue was purified by flash column chromatography on silica gel, using as eluent a gradient 100% DCM to 2% MeOH in DCM, to afford intermediate 20 (2 g, 81%).

Step 5. Intermediate 21

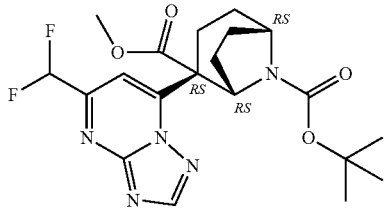 [SMILES: COC(=O)[C@]1(c2cc(C(F)F)nc3ncnn23)CC[C@H]2CC[C@@H]1N2C(=O)OC(C)(C)C]

LDA (54.3 mL, 108.7 mmol, 2 M in cyclohexane/ethylbenzene/THF) was added dropwise at −78° C. to −60° C. to a solution of intermediate 20 (24.4 g, 90.6 mmol) in anhydrous THF (363 mL), under an atmosphere of nitrogen. After the addition, the reaction mixture was warmed to −30° C. and stirred for 10 min, before being cooled back to −78° C. 7-Chloro-5-(difluoromethyl)-[1,2,4]triazolo[1,5-a]pyrimidine ([1340394-63-9], 18.5 g, 90.6 mmol) was dissolved in a minimum amount of THF and added dropwise with a syringe. The reaction mixture was stirred at −60° C. for 1 h, then the temperature was raised to RT and the reaction was quenched with a saturated aqueous NH$_4$Cl solution. The volatiles were evaporated in vacuo and the resulting residue partitioned between EtOAc and water. The layers were separated, then the aqueous layer was extracted 2×EtOAc. The combined OL were washed with brine, dried over MgSO$_4$, filtered and concentrated under reduced pressure. The resulting residue was crystallized from diethylether, to afford intermediate 47 (23.8 g, 60%). The filtrate was evaporated and the resulting residue was purified by flash column chromatography on silica gel, using as eluent a gradient 100% DCM to 2% MeOH in DCM, to afford intermediate 21 (2 g, 5%), after recrystallization from diethylether.

Step 6. Intermediate 16, Intermediate 16A and Intermediate 16B

INTERMEDIATE 16

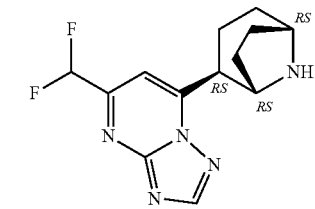

INTERMEDIATE 16A

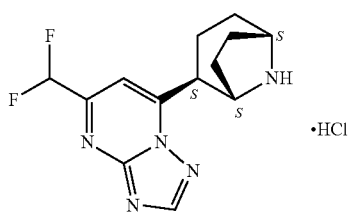
·HCl

INTERMEDIATE 16B

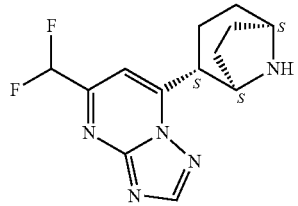

Intermediate 21 (25.8 g, 58.9 mmol) was stirred in a concentrated HCl solution (266 mL, 3.19 mol, 37% in H$_2$O) at 150° C. overnight. The volatiles were evaporated in vacuo and the resulting residue was co-evaporated twice with toluene. The product was treated with a saturated aqueous NaHCO$_3$ solution until basic pH. The aqueous layer was extracted with DCM, then the organic layer was dried on MgSO$_4$, filtered and evaporated under reduced pressure. The resulting residue was purified by flash column chromatography on silica gel, using as eluent a gradient 100% DCM to 8% MeOH/NH$_3$ in DCM, to afford the intermediate 16 as a racemic mixture (13 g, 79%). This material was purified via Prep SFC (Stationary phase: Chiralpak Diacel AD 20×250 mm, Mobile phase: CO$_2$, EtOH+0.4 iPrNH$_2$). The 1S,4S, 5S-enantiomer was converted to its HCl salt and recrystallized from CH$_3$CN to provide intermediate 16a (5.58 g, 30%, Rt=2.91 min, [c]$^{20}$D=−66.6 (c=0.48, DMF)).

B-Synthesis of Final Compounds

Compounds 1, 1a and 1B

Co. No. 1

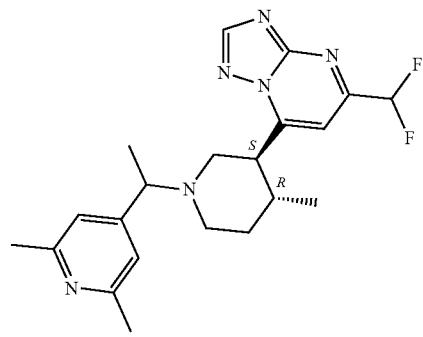

Co. No. 1a

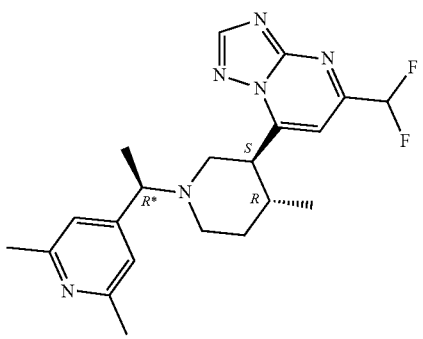

-continued

Co. No. 1b

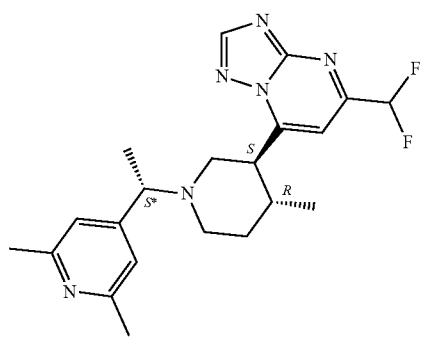

Et₃N [121-44-8] (643.574 μL, 0.728 g/mL, 4.63 mmol) was added to a stirred solution of intermediate 9b (401.811 mg, 1.323 mmol) in DMF [68-12-2] (16.928 mL, 0.944 g/mL) at 0° C. under N₂ atmosphere. The resulting mixture was stirred for 15 min and then a solution of intermediate 15 (crude material, 455 mg, 1.984 mmol) in DMF [68-12-2] (5 mL, 0.944 g/mL) was added. The r.m. was allowed to warm to r.t. and then stirred for another 72 h at r.t. After this time it was quenched with water and extracted with EtOAc. The combined organic layer was dried over MgSO₄, filtered and evaporated in vacuo. Crude compound 1 was purified by flash column chromatography on silica gel, using as eluent a gradient DCM-MeOH (9:1, v/v)/DCM, 0/100 to 10/90). The desired fractions were collected and concentrated in vacuo. Compound 1 (254 mg) was separated in the two diastereomers by SFC, using as stationary phase: Chiralpak Diacel AD 20×250 mm and as mobile phase: CO₂, iPrOH+ 0.4 iPrNH₂. Two fractions were collected and which were each triturated from a mixture of DCM and DIPE (1/1, v/v), to give the title compounds: 5-(difluoromethyl)-7-[(3 S,4R)-1-[(1R*)-1-(2,6-dimethyl-4-pyridyl)ethyl]-4-methyl-3-piperidyl]-[1,2,4]triazolo[1,5-a]pyrimidine (compound 1a) (100 mg, 18.87%) as an off-white solid and 5-(difluoromethyl)-7-[(3 S,4R)-1-[(1S*)-1-(2,6-dimethyl-4-pyridyl)ethyl]-4-methyl-3-piperidyl]-[1,2,4]triazolo[1,5-a]pyrimidine (compound 1b) (95 mg, 17.93%) as an off-white solid.

By using an analogous procedure to the one reported for the synthesis of compounds 1, 1a and 1b, starting from the corresponding prepared, known or commercially available alcohols or benzyl halides the following examples were obtained.

TABLE 1a

| Co. No. | Structure | Prepared from | Yield (%) |
|---|---|---|---|
| 2 | 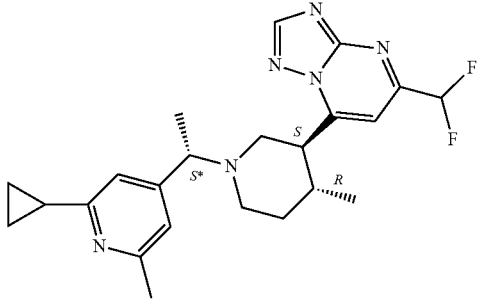 | I-12 | 13.35 |
| 3 | 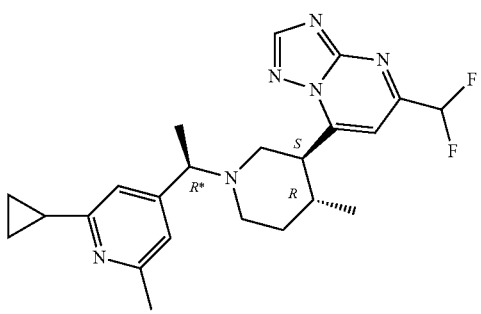 | I-12 | 12.65 |
| 4 | 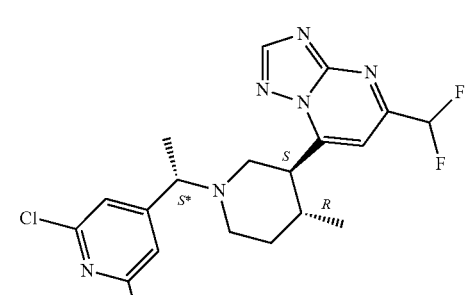 | I-14 | 1.9 |

TABLE 1a-continued

| Co. No. | Structure | Prepared from | Yield (%) |
|---|---|---|---|
| 5 | 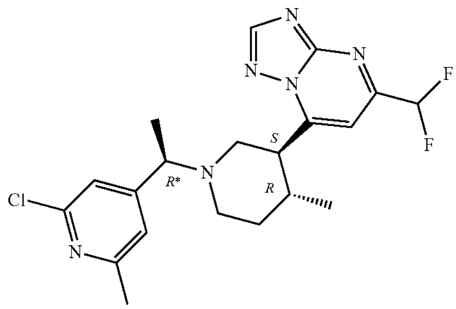 | I-14 | 1.9 |
| 6 | 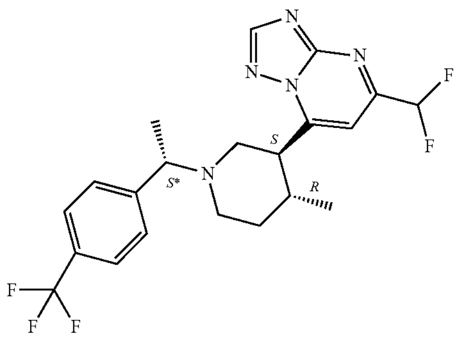 | 1-[4-(trifluoromethyl)phenyl]ethanol [1737-26-4] | 20.28 |
| 7 | 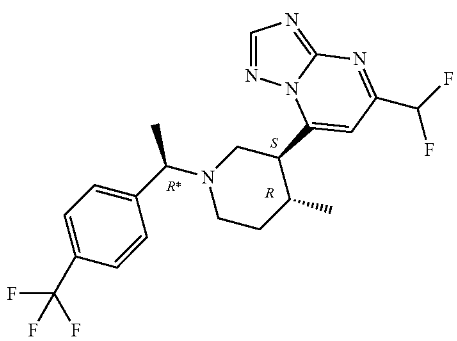 | 1-[4-(trifluoromethyl)phenyl]ethanol [1737-26-4] | 19.94 |
| 8 | 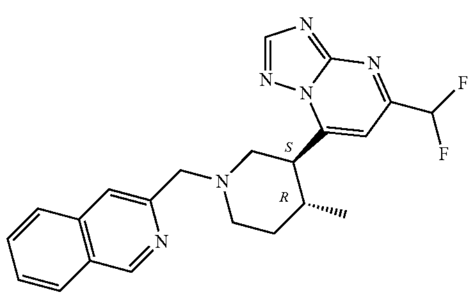 | 3-(bromomethyl)isoquinoline [1125-80-0] | 52.37 |
| 9 | 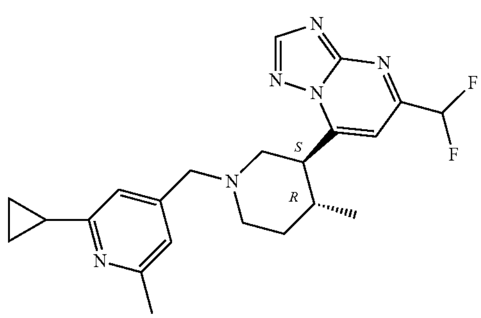 | I-13 | 31 |

TABLE 1a-continued
| Co. No. | Structure | Prepared from | Yield (%) |
|---|---|---|---|
| 10 | 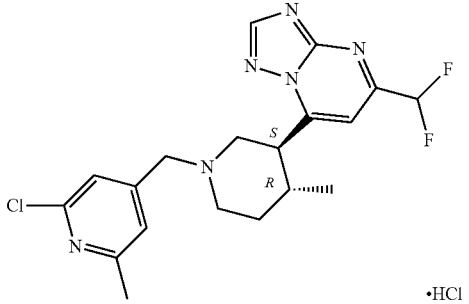 •HCl | 2-chloro-4-(chloromethyl)-6-methyl-pyridine [162046-59-5] | 60 |
| 11 | 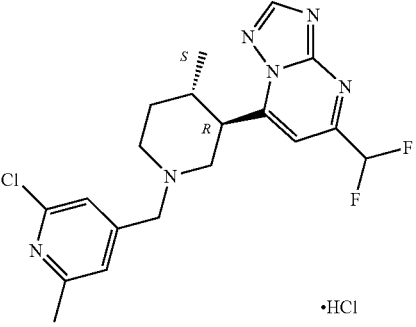 •HCl | 2-chloro-4-(chloromethyl)-6-methylpyridine [162046-59-5] | 35 |
| 12 | 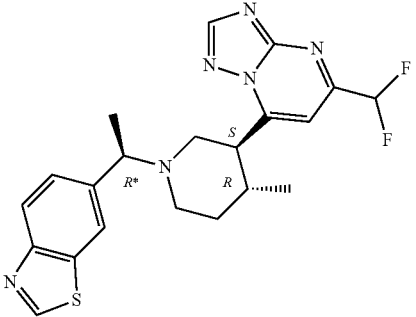 | 1-(1,3-benzothiazol-6-yl)ethanol [181820-06-4] | 38 |
| 13 | 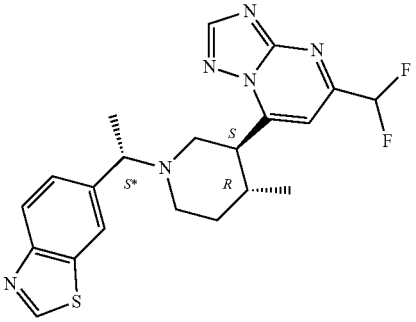 | 1-(1,3-benzothiazol-6-yl)ethanol [181820-06-4] | 36 |

TABLE 1a-continued

| Co. No. | Structure | Prepared from | Yield (%) |
|---|---|---|---|
| 14 | 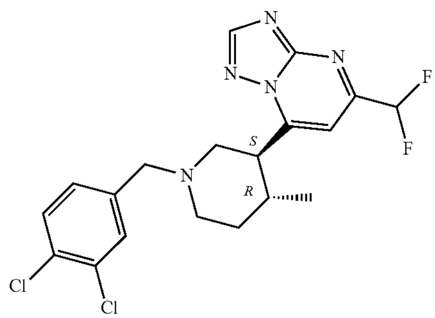 | 3,4-dichlorobenzyl bromide [18880-04-1] | 25 |
| 15 | 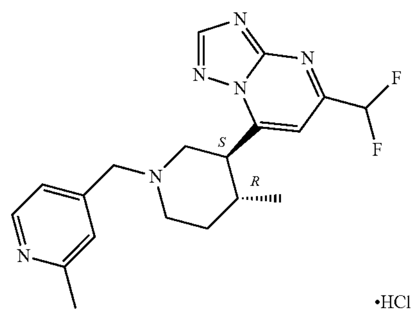 | 4-(chloromethyl)-2-methylpyridine hydrochloride [75523-42-1] | 77 |
| 16 | 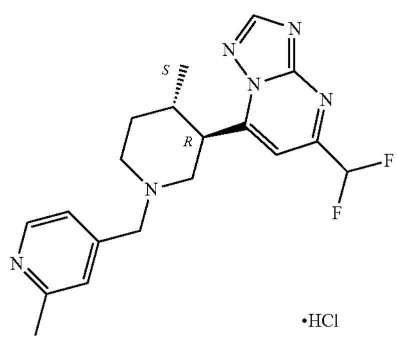 | 4-(chloromethyl)-2-methylpyridine hydrochloride salt [75523-42-1] | 76 |
| 17 | 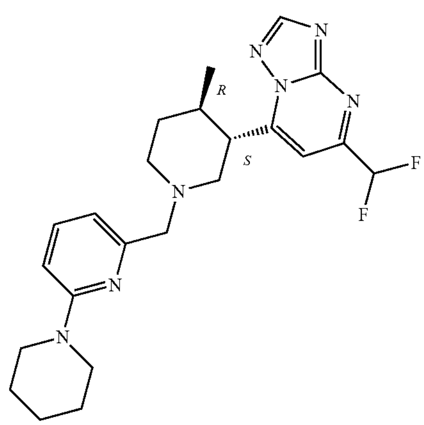 | (6-piperidinopyrid-2-yl)methanol, [869901-07-5] | 23 |

TABLE 1a-continued

| Co. No. | Structure | Prepared from | Yield (%) |
|---|---|---|---|
| 18 | 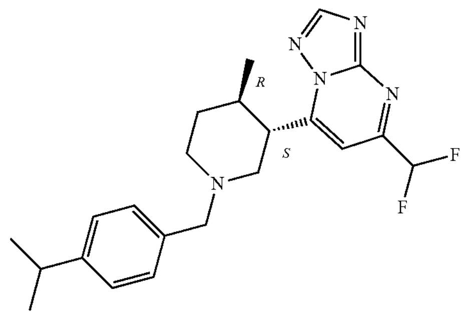 | 4-isopropylbenzyl bromide, [2051-99-2] | 51 |
| 19 | 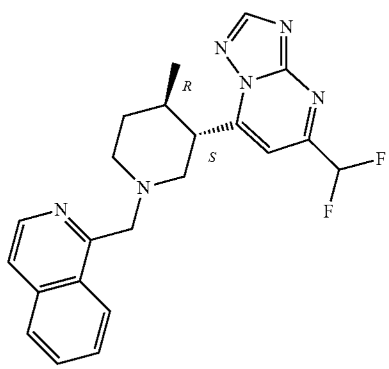 | 1-bromomethyl isoquinoline [74417-44-0] | 52 |
| 20 | 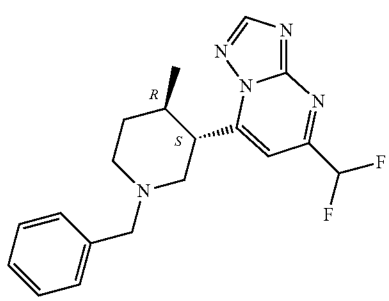 | Benzyl bromide | 55 |
| 21 | 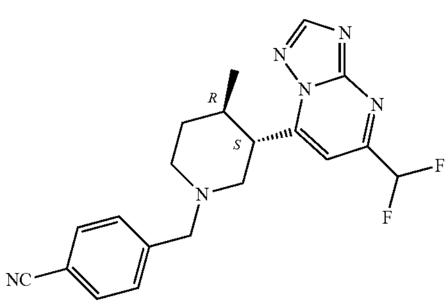 | 4-(chloromethyl)benzonitrile [874-86-2] | 46 |

TABLE 1a-continued

| Co. No. | Structure | Prepared from | Yield (%) |
|---|---|---|---|
| 22 | 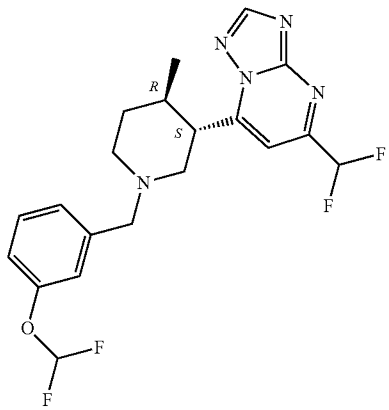 | 3-difluoromethoxybenzyl bromide [72768-95-7] | 21.5 |
| 23 | 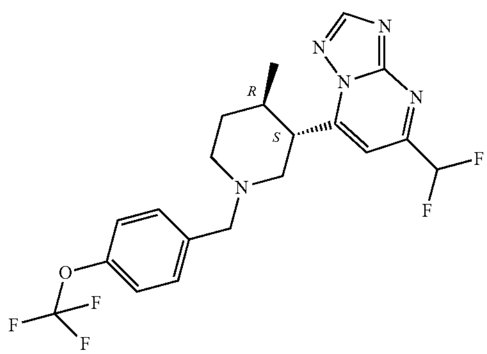 | 4-(trifluoromethoxy)benzyl bromoide [50824-05-0] | 55 |
| 24 | ·HCl | 3-(trifluoromethoxy)benzyl bromide [159689-88-0] | 8 |
| 25 | 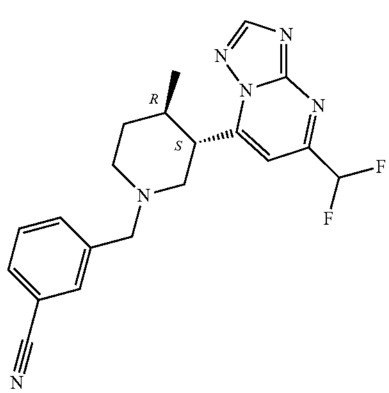 | 6-chloromethyl-2-cyanopyridine [135450-23-6] | 19 |

TABLE 1a-continued

| Co. No. | Structure | Prepared from | Yield (%) |
|---|---|---|---|
| 26 | (structure) ·HCl | 4-(bromomethyl) tetrahydropyran | 41 |
| 27 | (structure) ·HCl | 4-(bromomethyl) tetrahydropyran [125552-89-8] | 39 |
| 28 | (structure) | 2-chloro-4-(chloromethyl)-6-methylpyridine [162046-59-5] | 53 |
| 29 | (structure) | 1-bromo-2-methylpropane [78-77-3] | 37 |
| 30 | (structure) | 3-trifluoromethyl-4-fluorobenzyl chloride [67515-62-2] | 30 |

TABLE 1a-continued

| Co. No. | Structure | Prepared from | Yield (%) |
|---|---|---|---|
| 56 | 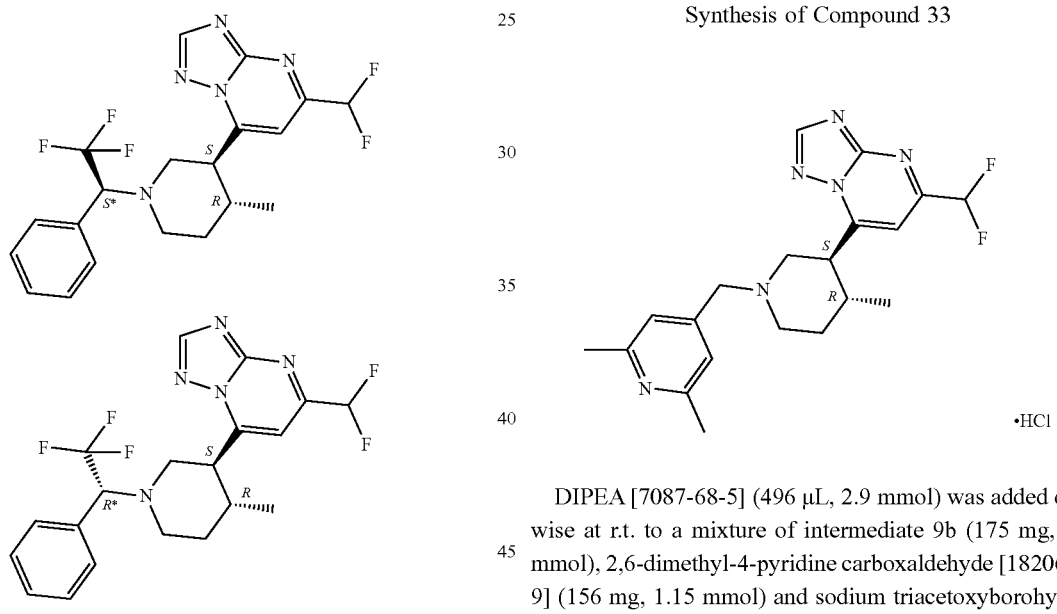·HCl | I-16a<br>3-(difluoromethoxy)benzyl bromide<br>[72768-95-7] | 49.5 |

Synthesis of Compounds 31 and 32

Intermediate 9b (174.442 mg, 0.574 mmol) was dissolved in anhydrous DCM (5 mL), 5 under a $N_2$ atmosphere. $Et_3N$ (0.08 mL, 0.728 g/mL, 0.57 mmol) was added and the resulting mixture stirred for 10 min prior to the addition of 2,2,2-trifluoro-1-phenyl-ethanone [434-45-7] (100 mg, 0.574 mmol), titanium tetrachloride (0.03 mL, 0.29 mmol) and $Et_3N$ (0.24 mL, 1.72 mmol). The r.m. was stirred for 16 h at r.t. A solution of sodium cyanoborohydride (114 mg, 1.72 mmol) in MeOH (2 mL) was added and the resulting mixture stirred 15 min at r.t., then treated with an aq. NaOH (1 N, 2 mL) solution and extracted thrice with EtOAc. The combined organic layers were dried over $MgSO_4$, filtered and evaporated in vacuo. The resulting residue was purified via Prep HPLC (Stationary phase: RP XBridge Prep $C_{18}$ ODB—5 μm, 30×250 mm, Mobile phase: 0.25% $NH_4HCO_3$ solution in water, $CH_3CN$) to give compound 32 (6.6 mg, 2.7%) and compound 31 (7.4 mg, 3%).

Synthesis of Compound 33

DIPEA [7087-68-5] (496 μL, 2.9 mmol) was added dropwise at r.t. to a mixture of intermediate 9b (175 mg, 0.58 mmol), 2,6-dimethyl-4-pyridine carboxaldehyde [18206-06-9] (156 mg, 1.15 mmol) and sodium triacetoxyborohydride [56553-60-7] (244 mg, 1.15 mmol) in DCM (5 mL). The reaction mixture was stirred at r.t. for 2 h, then it was quenched with water (1 mL) and stirred at r.t. for an additional hour. The resulting mixture was filtered over an Extrelute filter, which was washed with DCM (2×10 mL). The filtrate was evaporated in vacuo and the resulting residue was purified by Prep HPLC on (stationary Phase RP Vydac Denali C18—10 μm, 200 g, 5 cm; mobile phase: 0.25% $NH_4HCO_3$ solution in water, $CH_3CN$) to give the title compound as a free base. This material was treated with an ethereal solution of HCl, to give compound 33 (139 mg 57%) as white crystals.

By using an analogous procedure to the one reported for the synthesis of compound 33, starting from the corresponding known or commercially available aldehydes the following examples were obtained.

TABLE 1b

| Co. No. | Structure | Prepared from | Yield (%) |
|---|---|---|---|
| 34 | 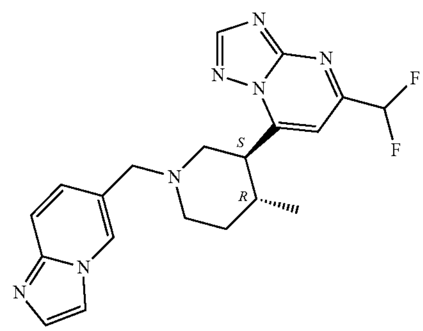 | imidazo[1,2-a]pyridine-6-carbaldehyde [116355-16-9] | 39 |
| 35 | ·HCl | 1-methyl-1H-indole-3-carbaldehyde [19012-03-4] | 43 |
| 36 | ·HCl | 4-chloro-3,5-dimethyl benzaldehyde [51719-64-3] | 82 |
| 37 | ·2 HCl | Benzofuran-2-carbaldehyde [4265-16-1] | 54 |
| 38 | ·HCl | Benzofuran-2-carbaldehyde [44265-16-1] | 63 |

TABLE 1b-continued

| Co. No. | Structure | Prepared from | Yield (%) |
|---|---|---|---|
| 39 | 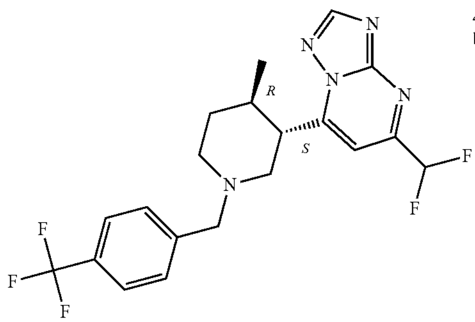 | 4-(trifluopromethyl)benzaldehyde | 55 |
| 40 | ·HCl | 3,4-difluorobenzaldehyde [34036-07-2] | 46 |
| 41 | ·HCl | 3,4-difluorobenzaldehyde [34036-07-2] | 77 |
| 42 | 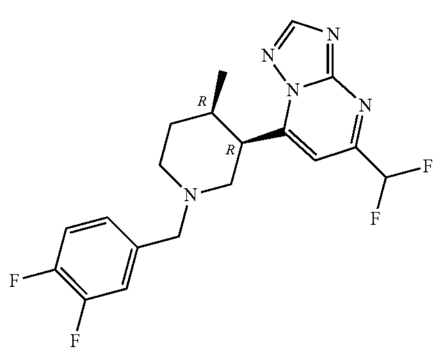 | 3,4-difluorobenzaldehyde [34036-07-2] | 3 |

TABLE 1b-continued

| Co. No. | Structure | Prepared from | Yield (%) |
|---|---|---|---|
| 43 | (structure) ·HCl | 4-methylthiophen-2-carboxaldehyde [6030-36-0] | 63 |
| 44 | (structure) ·2 HCl | Isonicotinaldehyde [872-85-5] | 52 |
| 45 | (structure) ·HCl | 2,4-dimethoxybenzaldehyde [613-45-6] | 58 |
| 46 | (structure) ·HCl | 2,4-dimethoxybenzaldehyde [613-45-6] | 41 |

TABLE 1b-continued
| Co. No. | Structure | Prepared from | Yield (%) |
|---|---|---|---|
| 47 | 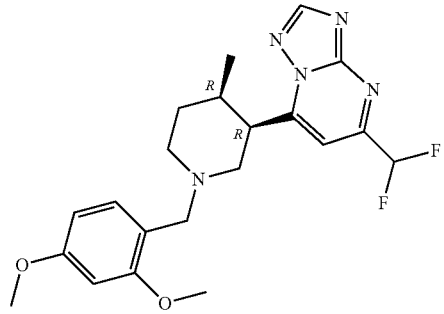 | 2,4-dimethoxybenzaldehyde [613-45-6] | 5 |
| 48 | 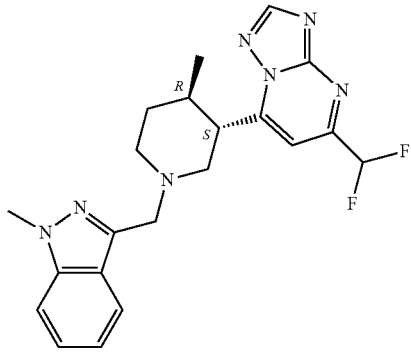 | 1-methyl-1H-indazole-3-carbaldehyde [4002-83-9] | 61 |
| 49 | 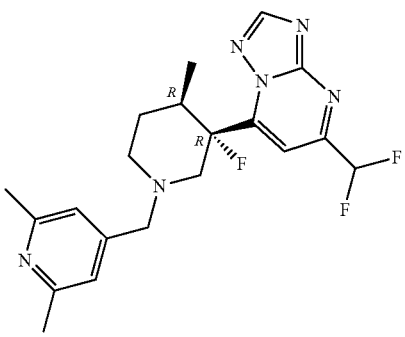 | 2,6-dimethylisonicotinaldehyde [18206-06-9] | 11 |
| 50 | 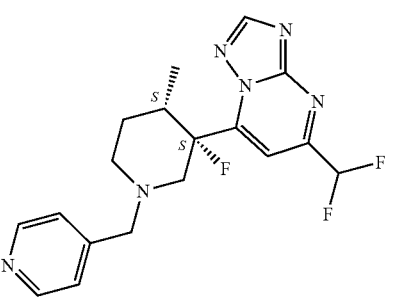 | 2,6-dimethylisonicotinaldehyde [18206-06-9] | 12 |

TABLE 1b-continued

| Co. No. | Structure | Prepared from | Yield (%) |
|---|---|---|---|
| 51 | 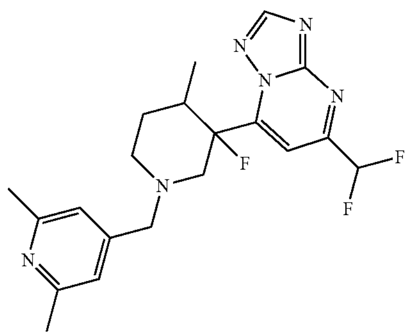 [SMILES: Cc1cc(CN2CCC(C)C(F)(c3cc(C(F)F)nc4ncnn34)C2)cc(C)n1] | 2,6-dimethylisonicotinaldehyde [18206-06-9] | 59 |
| 52 | •HCl | 1,3-dimethyl-1H-pyrazole-4-carbadehyde [25016-12-0] | 64 |
| 53 | •HCl | 2,4-dimethoxybenzaldehyde [613-45-6] | 80 |
| 54 | •HCl | 3,4-difluorobenzaldehyde [34036-07-2] | 83 |

TABLE 1b-continued

| Co. No. | Structure | Prepared from | Yield (%) |
|---|---|---|---|
| 55 | 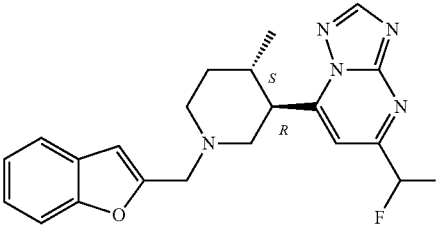 ·HCl | Benzo[b]furan-2-carboxaldehyde [4265-16-1] | 65 |
| 57 | 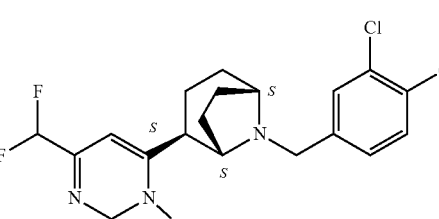 ·HCl | I-16 3,4-dichlorobenzaldehyde [6287-38-3] | 13 |

Analytical Part

Melting Points

Values are either peak values or melt ranges, and are obtained with experimental uncertainties that are commonly associated with this analytical method.

The melting point was determined with a DSC823e (Mettler-Toledo). The melting point was measured with a temperature gradient of 10° C./min. Maximum temperature was 300° C.

TABLE 2

| Co. No. | MP (° C.) |
|---|---|
| 1a | 141.46 |
| 17 | 137.52 |

Optical Rotation

Optical rotation was measured on a Perkin-Elmer 341 polarimeter with a sodium lamp and reported as follows: $[\alpha]°$ ($\lambda$, c g/100 ml, solvent, T° C.).

$[\alpha]_\lambda^T = (100\alpha)/(l \times c)$: where is the path length in dm and c is the concentration in g/100 ml for a sample at a temperature T (° C.) and a wavelength $\lambda$ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

TABLE 3

| Co. No. | OR |
|---|---|
| 28 | −8.14° (589 nm, c 0.295 w/v %, DMF, 20° C.) |

SFC-MS Methods

The SFC measurement was performed using an Analytical Supercritical fluid chromatography (SFC) system composed by a binary pump for delivering carbon dioxide ($CO_2$) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

| Method code | Column | Mobile phase | Gradient | Flow / Col T | Run time / BPR |
|---|---|---|---|---|---|
| 1 | Daicel Chiralpak ® AD-3 column (3.0 µm, 150 × 4.6 mm) | A: $CO_2$ B: iPrOH + 0.2% iPrNH$_2$ | 10%-50% B in 6 min, hold 3.5 min | 2.5 / 40 | 9.5 / 110 |
| 2 | Daicel (AD, OD, OJ, AS,)—H— column (5.0 µm, 250 × 4.6 mm) | A: $CO_2$ B: 3 different solvent for B used: (MeOH, EtOH, iPrOH) + 0.2% iPrNH$_2$ | 10%-40% B in 19.4 min, 40-50% in 2.00 min hold 3.6 min | 3 / 30 | 25 / 110 |
| 3 | Daicel Chiralpak ® OJ-3 column (3.0 µm, 150 × 4.6 mm) | A: $CO_2$ B: EtOH + 0.2% iPrNH$_2$ | 10%-50% B in 6 min, hold 3.5 min | 2.5 / 40 | 9.5 / 110 |

-continued

| Method code | Column | Mobile phase | Gradient | Flow / Col T | Run time / BPR |
|---|---|---|---|---|---|
| 4 | Daicel AS-H column (5.0 μm, 500 × 4.6 mm) | A: $CO_2$ B: iPrOH) + 0.2% iPrNH$_2$ | 10% B hold 15 min, 15-50% in 3.5 min hold 6.5 min | 3/30 | 25/110 |
| 5 | Daicel Chiralpak® AD-H column (5.0 μm, 250 × 4.6 mm) | A: $CO_2$ B: EtOH + 0.2% iPrNH$_2$ | 15% B hold 4 min, to 50% in 1 min hold 2 min | 5/40 | 7/110 |

TABLE 4B

ANALYTICAL SFC DATA-$R_t$ means retention time (in minutes), $[M + H]^+$ means the protonated mass of the compound, method refers to the method used for (SFC)MS analysis of enantiomerically pure compounds.

| Co. No. | $R_t$ (min) | $[M + H]^+$ | Method | Isomer Elution Order |
|---|---|---|---|---|
| 1a | 2.82 | no response | 1 | Enantiomer 1 |
| 1b | 3.11 | no response | 1 | Enantiomer 2 |
| 4 | 3.21 | 421 | 1 | Enantiomer 2 |
| 5 | 2.98 | 421 | 1 | Enantiomer 1 |
| 10 | 4.75 | 407 | 2 | N/A |
| 12 | 2.33 | 429 | 3 | Enantiomer 1 |
| 13 | 3.28 | 429 | 3 | Enantiomer 2 |
| 28 | 6.25 | 407 | 4 | Enantiomer 1 |
| 49 | 1.26 | 405 | 5 | Enantiomer 1 |
| 50 | 1.64 | 405 | 5 | Enantiomer 2 |

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times (Rt) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc. . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

TABLE 5A

LCMS Method codes (Flow expressed in mL/min; column temperature (T) in ° C.; Run time in minutes)

| Method code | Instrument | Column | Mobile phase | Gradient | Flow / Col T | Run time (min) |
|---|---|---|---|---|---|---|
| A | Waters: Acquity® UPLC® - DAD-SQD | Waters: BEH C18 (1.71 μm, 2.1 * 50 mm) | A: 10 mM $CH_3COONH_4$ in 95% $H_2O$ + 5% $CH_3CN$ B: $CH_3CN$ | From 95% A to 5% A in 1.3 min, held for 0.7 min. | 0.8/55 | 2 |
| B | Waters: Acquity® UPLC® - DAD and SQD | Waters: BEH C18 (1.71 μm, 2.1 * 50 mm) | A: 25 mM $CH_3COONH_4$ in 95% $H_2O$ + 5% $CH_3CN$ B: $CH_3CN$ | From 95% A to 5% A in 1.3 min, held for 0.7 min. | 0.8/55 | 2 |
| C | Waters: Acquity® UPLC® - DAD and SQD | Waters: HSS T3 (1.8 μm, 2.1 * 100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7/55 | 3.5 |

TABLE 5A-continued

LCMS Method codes (Flow expressed in mL/min; column temperature (T) in ° C.; Run time in minutes)

| Method code | Instrument | Column | Mobile phase | Gradient | Flow / Col T | Run time (min) |
|---|---|---|---|---|---|---|
| D | Waters: Alliance ® - DAD - ZQ and ELSD 2000 Alltech | Xterra MS C18 column (3.5 μm, 4.6 × 100 mm) | A: 10 mM CH$_3$COONH$_4$ in 95% H$_2$O + 5% CH$_3$CN B: CH$_3$CN C: CH$_3$OH D: (40% CH$_3$CN and 40% CH$_3$OH and 20% H$_2$O with 0.25% CH$_3$COOH | From 100% A to 1% A, 49% B and 50% C in 6.5 min, to 1% A and 99% B in 0.5 min, to 100% D in 1 min held for 1.0 min to 100% A in 0.5 min and held for 1.5 min. | 1.6 / 40 | 11 |
| E | Waters: Alliance ® - DAD - ZMD and CLND 8060 Antek | Waters: T3 C18 (3.5 μm, 4.6 * 100 mm) | A: 0.1% HCOOH + 5% CH3OH in H2O B: CH3OH | 100% A to 5% A in 9 min, held for 3.0 min to 100% A for 1.5 min. | 1.5 / 45 | 13.5 |

TABLE 5B

ANALYTICAL LCMS DATA-R$_t$ means retention time (in minutes), [M + H]$^+$ means the protonated mass of the compound, method refers to the method used for (LC)MS analysis.

| Co. No. | R$_t$ (min) | [M + H]$^+$ | [M + H]$^-$ | Method |
|---|---|---|---|---|
| 1a | 0.95 | 401 | 399 | A |
| 1b | 0.95 | 401 | 399 | A |
| 2 | 2.16 | 427 | 425 | C |
| 3 | 1.13 | 427 | 425 | A |
| 4 | 2.1 | 421 | 419 | C |
| 5 | 2.1 | 421 | 419 | C |
| 6 | 1.25 | 440 | 438 | A |
| 7 | 1.24 | 440 | 438 | A |
| 8 | 1.9 | 409 | 407 | C |
| 9 | 1.08 | 413 | 411 | A |
| 10 | 1.07 | 407 | — | A |
| 11 | 1.04 | 407 | 405 | A |
| 12 | 2 | 429 | 427 | C |
| 13 | 2 | 429 | 427 | C |
| 14 | 1.27 | 426 | 424 | A |
| 15 | 0.89 | 373 | — | A |
| 16 | 0.87 | 373 | 371 | A |
| 17 | 1.21 | 442 | 420 | A |
| 18 | 1.28 | 400 | 398 | A |
| 19 | 1.97 | 409 | 407 | C |
| 20 | 2.08 | 358 | 356 | C |
| 21 | 1.97 | 383 | 381 | C |
| 22 | 2.12 | 424 | 422 | C |
| 23 | 2.29 | 442 | 440 | C |
| 24 | 2.29 | 443 | 440 | C |
| 25 | 0.9 | 384 | 442 | A |
| 26 | 0.92 | 366 | — | A |
| 27 | 0.9 | 366 | 364 | A |
| 28 | 6.12 | 407 | 465 [M + CH$_3$COO]$^-$ | D |
| 29 | 1.08 | 324 | 322 | A |
| 30 | 2.25 | 444 | 442 | C |
| 31 | 1.2 | 426 | 424 | A |
| 32 | 2.22 | 426 | 424 | C |
| 33 | 1.02 | 387 | 385 | A |
| 34 | 0.8 | 398 | 396 | A |
| 35 | 1.05 | 411 | 409 | A |
| 36 | 1.34 | 420 | 418 | A |
| 37 | 5.87 | 384 | 382 | E |
| 38 | 1.14 | 398 | — | A |
| 39 | 2.27 | 427 | 424 | C |
| 40 | 1.17 | 394 | — | A |
| 41 | 1.13 | 394 | 392 | A |
| 42 | 1.24 | 394 | 392 | A |
| 43 | 1.16 | 378 | — | A |
| 44 | 1.65 | 359 | 357 | C |
| 45 | 1.05 | 418 | — | A |
| 46 | 1.05 | 418 | 416 | A |
| 47 | 1.19 | 418 | — | A |
| 48 | 0.99 | 412 | 410 | A |
| 49 | 1.86 | 405 | 463 [M + CH$_3$COO]$^-$ | C |
| 50 | 1.86 | 405 | 463 [M + CH$_3$COO]$^-$ | C |
| 51 | 1 | 405 | — | A |
| 52 | 0.78 | 376 | — | A |
| 53 | 1.18 | 418 | — | A |
| 54 | 1.2 | 394 | 452 | A |
| 55 | 1.11 | 398 | 396 | A |
| 56 | 1.15 | 436 | 434 | A |
| 57 | 1.31 | 438 | 436 | A |

Nuclear Magnetic Resonance (NMR)

The $^1$H NMR spectrum was recorded either on Bruker DPX-400 spectrometer with standard pulse sequences, operating at 400 MHz or on a Bruker DPX-360 operating at 360 MHz, using DMSO-d$_6$ (deuterated DMSO, dimethyl-d$_6$ sulfoxide) as solvents. Chemical shifts (δ) are reported in parts per million (ppm) relative to tetramethylsilane (TMS), which was used as internal standard Co. No. 1b: $^1$H NMR (360 MHz, CHLOROFORM-d) δ ppm 0.88 (br d, J=5.49 Hz, 3H); 1.35 (d, J=6.59 Hz, 3H);

1.51-1.68 (m, 1H); 1.90 (br d, J=10.61 Hz, 2H); 2.06-2.33 (m, 2H); 2.50 (s, 6H); 2.95-3.10 (m, 2H); 3.45 (q, J=6.59 Hz, 1H); 3.73 (br s, 1H); 6.66 (t, J=54.70 Hz, 1H); 6.93 (s, 2H); 7.27 (s, 1H); 8.55 (s, 1H).

Co. No. 3: $^1$H NMR (360 MHz, CHLOROFORM-d) δ ppm 0.85-0.90 (m, 3H) 0.95 (d, J=6.95 Hz, 4H) 1.34 (d, J=6.95 Hz, 3H) 1.60 (br d, J=10.98 Hz, 1H) 1.82-2.12 (m, 3H) 2.23 (td, J=11.43, 2.01 Hz, 2H) 2.44 (s, 3H) 2.94-3.11 (m, 2H) 3.41 (q, J=6.59 Hz, 1H) 3.73 (br s, 1H) 6.66 (t, J=54.70 Hz, 1H) 6.82 (s, 1H) 6.85 (s, 1H) 7.27 (s, 1H) 8.55 (s, 1H).

Co. No. 8: $^1$H NMR (400 MHz, DMSO-d$_6$ ON 100 CELCIUS DEGREES) δ ppm 0.84 (d, J=6.6 Hz, 3H) 1.55 (dtd, J=13.3, 11.1, 11.1, 4.0 Hz, 1H) 1.85 (dq, J=13.4, 3.5 Hz, 1H), 2.14-2.24 (m, 1 h), 2.42-2.48 (m, 1H), 2.61-2.70 (m, 1H), 2.97-3.06 (m, 1H), 3.17 (ddd, J=11.2, 3.5, 1.5 Hz, 1H), 3.71 (td, J=10.2, 3.7 Hz, 1H), 3.89 (s, 2H), 7.00 (t, J=54.4 Hz, 1H), 7.6 (s, 1H), 7.6-7.64 (m, 1H), 7.73 (ddd, J=8.2, 6.9, 1.2 Hz, 1H), 7.81 (s, 1H), 7.92 (d, J=8.4 Hz, 1H), 8.05 (d, J=8.4 Hz, 1H), 8.70 (s, 1H), 9.21 (s, 1H).

Co. No. 34 $^1$H NMR (360 MHz, DMSO-d$_6$) δ ppm 0.75 (br d, J=6.59 Hz, 3H) 1.39-1.51 (m, 1H) 1.81 (br dd, J=13.36, 3.48 Hz, 1H) 1.95-2.19 (m, 1H) 2.20-2.47 (m, 2H) 2.88-3.07 (m, 2H) 3.48-3.66 (m, 3H) 7.09 (t, J=54 Hz, 1H) 7.21 (dd, J=9.15, 1.46 Hz, 1H) 7.49-7.53 (m, 2H) 7.65 (s, 1H) 7.87 (s, 1H) 8.44 (s, 1H) 8.80 (s, 1H).

PHARMACOLOGICAL EXAMPLES

The compounds provided in the present invention are an inhibitors of PDE2, particularly of PDE2A. The results of testing the compounds in several pharmacological assays are shown below.

In Vitro Assay PDE2A

Human recombinant PDE2A (hPDE2A) was expressed in Sf9 cells using a recombinant rPDE10A baculovirus construct. Cells were harvested after 48 h of infection and the hPDE2A protein was purified by metal chelate chromatography on Ni-sepharose 6FF. Tested compounds were dissolved and diluted in 100% DMSO to a concentration 100 fold of the final concentration in the assay. Compound dilutions (0.4 µl) were added in 384 well plates to 20 µl of incubation buffer (50 mM Tris pH 7.8, 8.3 mM MgCl$_2$, 1.7 mM EGTA). 10 µl of hPDE2A enzyme in incubation buffer was added and the reaction was started by addition of 10 µl substrate to a final concentration of 10 µM cGMP and 0.01 µCi $^3$H-cGMP. The reaction was incubated for 45 minutes at room temperature. After incubation, the reaction was stopped with 20 µl of stop solution consisting of 17.8 mg/ml PDE SPA scintillation proximity assay) beads supplemented with 200 mM ZnCl$_2$. After sedimentation of the beads during 30 minutes the radioactivity was measured in a Perkin Elmer Topcount scintillation counter and results were expressed as cpm. For blanc values the enzyme was omitted from the reaction and replaced by incubation buffer. Control values were obtained by addition of a final concentration of 1% DMSO instead of compound. A best fit curve is fitted by a minimum sum of squares method to the plot of % of control value substracted with blanc value versus compound concentration and the half maximal inhibitory concentration (IC$_{50}$) value is derived from this curve.

In Vitro Assay PDE3A

Human recombinant PDE3A (hPDE3A) was supplied as a partially purified insect cell lysate by Scottish Biomedical, it was cloned from human brain and expressed in Sf9 cells. Tested compounds were dissolved and diluted in 100% DMSO to a concentration 100 fold of the final concentration in the assay. Compound dilutions (0.4 µl) were added in 384 well plates to 20 µl of incubation buffer (50 mM Tris pH 7.8, 8.3 mM MgCl$_2$, 1.7 mM EGTA). 10 µl of hPDE3A enzyme in incubation buffer was added and the reaction was started by addition of 10 µl substrate to a final concentration of 0.4 µM cAMP and 2.4 µCi/ml [$^3$H]-cAMP. The reaction was incubated for 60 min at room temperature. After incubation, the reaction was stopped with 20 µl of stop solution consisting of 17.8 mg/ml PDE SPA (scintillation proximity assay) beads supplemented with 200 mM ZnCl$_2$. After sedimentation of the beads during 30 min the radioactivity was measured in a Perkin Elmer Topcount scintillation counter and results were expressed as cpm. For blanc values the enzyme was omitted from the reaction and replaced by incubation buffer. Control values were obtained by addition of a final concentration of 1% DMSO instead of compound. A best fit curve is fitted by a minimum sum of squares method to the plot of % of control value substracted with blanc value versus compound concentration and the half maximal inhibitory concentration (IC$_{50}$) value is derived from this curve.

In Vitro Assay PDE10A

Rat recombinant PDE10A (rPDE10A2) was expressed in Sf9 cells using a recombinant rPDE10A baculovirus construct. Cells were harvested after 48 h of infection and the rPDE10A protein was purified by metal chelate chromatography on Ni-sepharose 6FF. Tested compounds were dissolved and diluted in 100% DMSO to a concentration 100 fold of the final concentration in the assay. Human recombinant PDE10A (hPDE2A) was expressed in Sf9 cells using a recombinant hPDE10A baculovirus that was made and amplified in house. Cells were harvested after 72 h of infection and the hPDE10A protein was purified by metal chelate chromatography on Ni-sepharose. Compound dilutions (0.4 µl) were added in 384 well plates to 20 µl of incubation buffer (50 mM Tris pH 7.8, 8.3 mM MgCl$_2$, 1.7 mM EGTA). 10 µl of rPDE10A or hPDE10A enzyme in incubation buffer was added and the reaction was started by addition of 10 µl substrate to a final concentration of 60 nM cAMP and 0.008 Ci $^3$H-cAMP. The reaction was incubated for 60 minutes at room temperature. After incubation, the reaction was stopped with 20 µl of stop solution consisting of 17.8 mg/ml PDE SPA (scintillation proximity assay) beads. After sedimentation of the beads during 30 minutes the radioactivity was measured in a Perkin Elmer Topcount scintillation counter and results were expressed as cpm. For blanc values the enzyme was omitted from the reaction and replaced by incubation buffer. Control values were obtained by addition of a final concentration of 1% DMSO instead of compound. A best fit curve is fitted by a minimum sum of squares method to the plot of % of control value substracted with blanc value versus compound concentration and the half maximal inhibitory concentration (IC$_{50}$) value is derived from this curve.

TABLE 6

| Co. No. | hPDE2A pIC$_{50}$ | hPDE2A E$_{max}$ | hPDE3B pIC$_{50}$ | hPDE3B E$_{max}$ | hPDE10A2 or rPDE10A2(&) pIC$_{50}$ | hPDE10A2 or rPDE10A2 E$_{max}$ |
|---|---|---|---|---|---|---|
| 1 | 7.68 | 100 | <5 | 45 | 5.53 | 74 |
| 1a | 6.99 | 99 | <5 | 34 | 5.25 | 64 |
| 1b | 7.93 | 100 | <5 | 19 | 5.54 | 80 |
| 2 | 7.06 | 99 | <5 | 29 | 5.53 | 78 |
| 3 | 7.87 | 100 | <5 | 19 | 5.9 | 91 |
| 4 | 8.11 | 99 | <5 | 45 | 5.96 | 88 |
| 5 | 7.11 | 100 | 5.13 | 55 | 5.82 | 87 |
| 6 | 6.75 | 99 | <5 | 37 | 5.2 | 68 |
| 7 | 6.99 | 98 | 5.08 | 57 | 5.11 | 47 |
| 8 | 8.07 | 100 | 5.09 | 61 | 5.83 | 85 |
| 9 | 8.28 | 100 | <5 | 34 | 5.8 | 83 |
| 10 | 7.61 | 96 | <5 | 19 | 5.8 | 82 |
| 11 | 5.41 | 19 | ~5.4 | 71 | ~4.99 | 47 |
| 12 | 7.35 | 99 | ~5.07 | 54 | 5.69 | 86 |
| 13 | 7.23 | 98 | ~5.02 | 47 | 5.83 | 85 |
| 14 | 7.25 | 102 | <5 | 39 | 5.64 | 80 |
| 15 | 7.02 | 95 | <4.52 | 17 | ~5 | 45 |
| 16 | 5.23 | 4 | <5 | 23 | <5 | 10 |
| 17 | 6.71 | 100 | <5 | 41 | <5 | 49 |
| 18 | 6.55 | 98 | 5.1 | 60 | 5.11 | 56 |
| 19 | 6.49 | 96 | <5 | 35 | 5.07 | 58 |
| 20 | 6.34 | 97 | <5 | 23 | <5 | 26 |
| 21 | 6.33 | 97 | <5 | 24 | ~5 | 48 |
| 22 | 6.25 | 95 | <5 | 42 | 5.11 | 61 |
| 23 | 6.24 | 97 | 5.14 | 49 | 5.16 | 62 |
| 24 | 6.16 | 96 | <5 | 31 | 5.14 | 58 |
| 25 | 5.99 | 92 | <5 | 12 | <5 | 28 |
| 26 | ~5.51 | 27 | <5 | 12 | <5 | 12 |
| 27 | ~5.31 | 20 | <5 | 3 | <5 | 11 |
| 28 | 5.25 | 16 | <5 | 10 | <5 (r) | 7.2 (r) |
| 29 | ~5.06 | 3 | <5 | −14 | <5 | 3 |
| 30 | 6.31 | 99 | <5 | 21 | 5.1 | 55 |
| 31 | 5.81 | 91 | <5 | 24 | 5.01 | 51 |
| 32 | 6.07 | 96 | <5 | 35 | <5 | 46 |
| 33 | 7.65 | 96 | <5 | 8 | 5.39 | 72 |
| 34 | 7.64 | 91 | <5 | 18 | 5.33 | 67 |
| 35 | 7.32 | 102 | <5 | 22 | 5.12 | 53 |
| 36 | 7.25 | 100 | <5 | 43 | 5.43 | 82 |
| 37 | 6.7 | 81 | 5.92 | 88 | 5.98 (r) | 50.705 (r) |
| 38 | 6.79 | 88 | <5 | 28 | 5.33 | 69 |
| 39 | 6.77 | 99 | <5 | 46 | 5.21 | 65 |
| 40 | 5.95 | 42 | <5 | 10 | <5 | 35 |
| 41 | 5.71 | 33 | <5 | 20 | <5 | 15 |
| 42 | 5.47 | 22 | <5 | 19 | <5 | 45 |
| 43 | 6.46 | 77 | <5 | 0 | 5.16 | 44 |
| 45 | 6.02 | 49 | <5 | 6 | <5 | 37 |
| 46 | 5.14 | 9 | <5 | 17 | <5 | −6 |
| 47 | ~5.46 | 25 | <5 | 27 | <5 | 37 |
| 48 | 6.01 | 96 | <5 | 23 | <5 | 37 |
| 49 | 5.67 | 86 | <5 | 17 | <5 | 12 |
| 50 | 5.42 | 75 | ~5 | 53 | <5 | 13 |
| 51 | 5.53 | 91 | 5.11 | 67 | <5 | 28 |
| 52 | ~5.63 | 31 | <5 | 1 | <5 | 9 |
| 53 | 5.16 | 14 | <5 | 3 | <5 | 0 |
| 54 | ~5.05 | 15 | <5 | 5 | <5 | 9 |
| 55 | 5.65 | 25 | <5 | 40 | <5 | 12 |
| 56 | 6.28 | 97 | <5 | 26 | <5 | 43 |
| 57 | 6.98 | 100 | <5 | 35 | 5.1 | 58 |

($^{\&}$) The data reported is in the human clon unless otherwise indicated that it is in rat (r).

PDE2 Occupancy by Test Compounds
Methods

Occupancy of PDE2A was evaluated by ex-vivo autoradiography using [$^3$H]B-17a (described in WO2013/000924) as radioligand (compound 12 in Buijnster et al., (2014). Structure-Based Design of a Potent, Selective, and Brain Penetrating PDE2 Inhibitor with Demonstrated Target Engagement. ACS Med Chem Lett. 5(9):1049-53.) Male Wistar rats (200-250 g) were treated by oral administration of vehicle or increasing doses of [$^3$H]B-17a and killed one h after. Brains were immediately removed from the skull and rapidly frozen in dry-ice cooled 2-methylbutane (−40° C.). Twenty μm-thick striatal sections were cut using a Leica CM 3050 cryostat-microtome (van Hopplynus, Belgium), thaw-mounted on microscope slides (SuperFrost Plus Slides, LaboNord, France) and stored at −20° C. until use.

After thawing, sections were dried under a cold stream of air and incubated for one minute with 30 nM [$^3$H]B-17a in Tris-HCl (50 mM, pH7.4) containing 0.3% BSA. Brain sections from drug-treated and vehicle-treated animals were incubated in parallel. Non-specific binding was measured on cerebellar sections, a brain area which does not contain the PDE2A enzyme. After incubation, the excess of [$^3$H]B-17a was washed off in ice-cold buffer 2 times 10 minutes, followed by a quick dip in distilled water. The sections were then dried under a stream of cold air.

Brain sections were loaded in a β-imager (Biospace, Paris) for 4 h and radioactivity emerging from delineated brain area was quantified using the Beta vision program (Biospace, Paris). Specific binding was determined as the difference between total binding in the striatum and non-specific binding in the cerebellum. Percentage receptor occupancy of the drug administered to the animal corresponded to 100% minus the percentage receptor labeled in the treated animal. For the determination of $ED_{50}$-values, the percentage of receptor occupancy was plotted against dose and the sigmoidal log dose-effect curve of best fit was calculated by non-linear regression analysis, using the GraphPad Prism program. $ED_{50}$s (the drug dose producing 50% receptor occupancy) with 95% confidence limits were calculated from the dose-response curves.

TABLE 7

| Co. No. | PDE2 occupancy at 10 mg/kg | Route PDE2 occupancy at 10 mg/kg |
|---|---|---|
| 1b | 42 | SC |
| 3 | 21 | PO |
| 8 | 0 | SC |
| 33 | 37 | SC |
| 34 | 0 | PO |
| 36 | 0 | PO |

PO = oral;
SC = subcutaneous

Reasonable variations are not to be regarded as a departure from the scope of the invention. It will be obvious that the thus described invention may be varied in many ways by those skilled in the art.

The invention claimed is:

1. A compound having the Formula (IA)

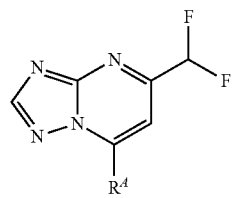

(IA)

or a stereoisomeric form thereof, wherein
$R^A$ represents a radical (b):

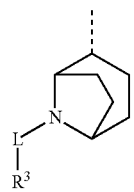

wherein
L is selected from the group consisting of $>CH_2$, $>CH(CH_3)$, $>CH(CF_3)$ and $—CH_2CH_2—$; and
$R^3$ is selected from the group consisting of $C_{1-4}$alkyl; aryl and Het; wherein aryl represents a phenyl optionally substituted with one, two or three substituents, each independently selected from the group consisting of halo; —CN; $C_{1-4}$alkyl optionally substituted with 1, 2 or 3 independently selected halo substituents; and $C_{1-4}$alkyloxy optionally substituted with 1, 2 or 3 independently selected halo substituents;

Het is (a) a 5-membered heteroaryl radical selected from thiophenyl and pyrazolyl, each optionally substituted with 1 or 2 independently selected $C_{1-4}$alkyl substituents; or (b) a 6-membered heteroaryl radical selected from pyridyl and pyrimidinyl, each optionally substituted with 1 or 2 substituents, each independently selected from the group consisting of halo; —CN; $C_{1-4}$alkyl optionally substituted with 1, 2 or 3 independently selected halo substituents; $C_{3-6}$cycloalkyl; and 1-piperidinyl; or (c) a 9- or 10-membered heteroaryl radical selected from the group consisting of 1H-indolyl, benzofuranyl, 1H-indazolyl, 1,3-benzothiazolyl, imidazo[1,2,-a]pyridinyl, and isoquinolinyl; each optionally substituted with a $C_{1-4}$alkyl substituent; or (d) tetrahydropyranyl;

or a pharmaceutically acceptable salt or a solvate thereof.

2. The compound according to claim 1, having the Formula (I-b)

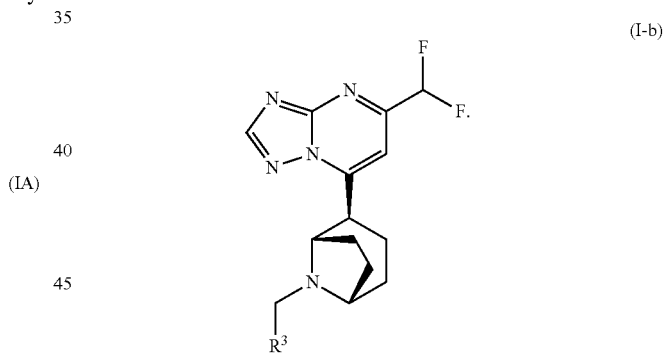

(I-b)

3. The compound according to claim 2, wherein $R^3$ is phenyl optionally substituted with one, two or three substituents, each independently selected from the group consisting of halo; —CN; $C_{1-4}$alkyl optionally substituted with 1, 2 or 3 independently selected halo substituents; and $C_{1-4}$alkyloxy optionally substituted with 1, 2 or 3 independently selected halo substituents.

4. A pharmaceutical composition comprising a therapeutically effective amount of a compound according to claim 1 and a pharmaceutically acceptable carrier.

5. A process for preparing a pharmaceutical composition, characterized in that a pharmaceutically acceptable carrier is intimately mixed with a therapeutically effective amount of a compound according to claim 1.

6. A compound according to claim 1 selected from the group consisting of:
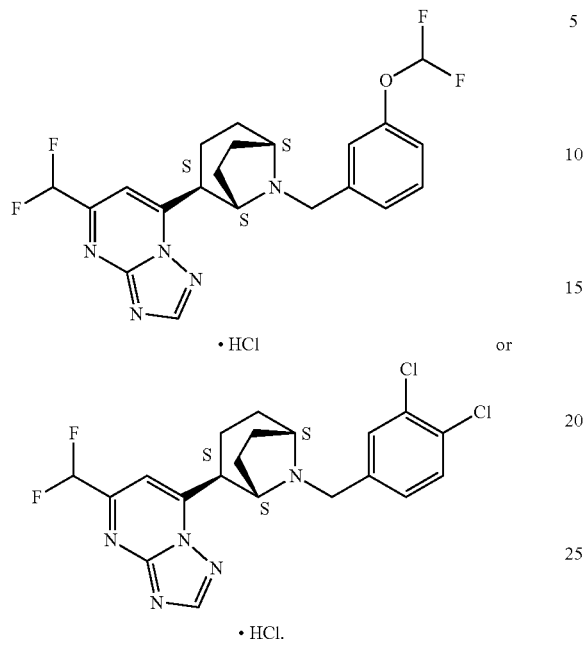
* * * * *